United States Patent [19]

Sternberg et al.

[11] Patent Number: 5,209,920

[45] Date of Patent: * May 11, 1993

[54] EVALUATIVE MEANS FOR DETECTING INFLAMMATORY REACTIVITY

[75] Inventors: Esther M. Sternberg, Chevy Chase; Ronald L. Wilder, Derwood, both of Md.; Philip W. Gold, Washington, D.C.; George P. Chrousos, Bethesda, Md.

[73] Assignee: The United States of America as represented by the United States Department of Health and Human Services, Washington, D.C.

[*] Notice: The portion of the term of this patent subsequent to Apr. 9, 2008 has been disclaimed.

[21] Appl. No.: 412,294

[22] Filed: Sep. 25, 1989

Related U.S. Application Data

[63] Continuation-in-part of Ser. No. 365,735, Jun. 14, 1989, which is a continuation-in-part of Ser. No. 277,708, Nov. 30, 1988, Pat. No. 5,006,330.

[51] Int. Cl.$^5$ .................. G01N 1/00; G01N 33/48; A61K 37/60; A61K 45/05
[52] U.S. Cl. ........................ 424/9; 424/85.1; 424/85.2; 424/85.4; 424/85.5; 424/85.6; 424/85.7; 514/805; 514/825; 514/885.1; 514/886; 514/884; 435/975; 436/2; 206/569
[58] Field of Search .............. 424/2, 9, 85.1, 85.2, 424/85.4, 85.5, 85.6, 85.7; 514/825, 887, 885, 886, 815; 435/975; 436/2; 206/569

[56] References Cited

U.S. PATENT DOCUMENTS 5,006,330 4/1991 Sternberg et al. ............... 514/825

OTHER PUBLICATIONS

Gross et al. "A Radio immunoassay for Plasma Corticosterone" Steroids, 20, 1972, pp. 681–695.

*Primary Examiner*—Nathan M. Nutter
*Attorney, Agent, or Firm*—NIH/Office of Technology Transfer

[57] ABSTRACT

Inbred Lewis (LEW/N) female rats develop an arthritis in response to Group A streptococcal cell wall peptidoglycanpolysaccharide (SCW) which mimics human rheumatoid arthritis. Histocompatible Fischer (F344/N) rats, on the other hand, do not develop arthritis in response to the same SCW stimulus. To evaluate this difference in inflammatory reactivity between the two strains, the function of the hypothalamic-pituitary-adrenal axis and its ability to modulate the development of the inflammatory response was studied. It has been found that, in contrast to F344/N rats, LEW/N rats had markedly impaired plasma ACTH and corticosterone responses to SCW, recombinant human Interleukin-1 alpha (IL-1 alpha), the serotonin agonist, quipazine, and synthetic rat corticotropin-releasing hormone (CRH). In addition, LEW/N rats compared to F344/N rats had smaller adrenal glands and larger thymuses. Treatment of LEW/N rats with replacement doses of dexamethasone decreased the severity of their SCW-induced arthritis. Conversely, treatment of F344/N rats with the glucocorticoid receptor antagonist, RU 486, or the serotonin (5-HT$_2$) antagonist, LY53857, was associated with development of severe inflammatory disease, including arthritis, in response to SCW. These findings support the concept that susceptibility of LEW/N rats to SCW arthritis is related to abnormal hypothalamic-pituitary-adrenal (HPA) axis responsiveness to inflammatory and other stress mediators and that resistance of F344/N rats to SCW arthritis is regulated by an intact HPA axis-immune system feedback loop.

41 Claims, 9 Drawing Sheets

EVALUATIVE MEANS FOR DETECTING INFLAMMATORY REACTIVITY

CROSS-REFERENCE TO RELATED APPLICATIONS

This application is a Continuation-in-Part of copending application Ser. No. 07/365,735, filed Jun. 14, 1989, which is a CIP of application Ser. No. 07/277,708, filed on Nov. 30, 1988, now U.S. Pat. No. 5,006,330 issued Apr. 9, 1991.

BACKGROUND OF THE INVENTION

The present invention relates to a diagnostic test for testing the susceptibility of individuals to inflammatory diseases such as rheumatoid arthritis and also to potential treatment of arthritis with therapeutic agents directed at the central nervous system (CNS), designed to by-pass the CNS defect.

SUMMARY OF THE INVENTION

It is an object of the present invention to provide a method for testing mammals for susceptibility to inflammatory diseases. In its broadest aspect, the method comprises the steps of administering to a mammal a compound which is effective in stimulating the hypothalamic-pituitary-adrenal (HPA) axis and measuring the level of hormones secreted by the pituitary and adrenal glands of the mammal. In a more specific aspect, the method comprises the steps of administering to a mammal a compound selected from the group consisting of cytokines, cell growth factors, neuroendocrine hormones such as corticotropin releasing hormone (CRH) or arginine vasopressin (AVP), biogenic amines, agonists of biogenic amines, antagonists of biogenic amines, analogues of biogenic amines, monoamine oxidase inhibitors and biogenic uptake inhibitors or glucocorticoid receptor antagonists and measuring the level of glucocorticoids or adrenocorticotropic hormone (ACTH) in the blood plasma of the mammal. The substance which is administered should not be the same as the material which is measured.

The invention is useful as a model in the study of the mammalian autoimmune diseases. Laboratory animals which may serve as a good model in studying human systems include rats, mice, guinea pigs, rabbits and chickens. However, an ultimate objective of this invention is to provide a method for diagnosing the susceptibility of humans to inflammatory diseases.

The hormones to be measured should be hormones which are secreted in increased levels by normal individuals when the compound is administered to the individual but which are not secreted in such high levels after administration of the compound in individuals having an inflammatory disease or susceptibility to an inflammatory disease. Hormones secreted by the pituitary and adrenal glands which can be measured include glucocorticoids such as corticosterone, cortisol, and ACTH. Other hormones which can be measured include CRH, prolactin, arginine vasopressin (AVP), growth hormone (GH), thyroid stimulating hormone (TSH), and endorphins/enkephalins.

The compound which is used in the test is preferably administered intravenously (i.v.), however, other modes of administration such as subcutaneously (s.c.) or orally (p.o.) may be used. The compound is administered together with a suitable non-toxic pharmaceutically acceptable carrier in an amount sufficient to stimulate the hypothalamic-pituitary-adrenal axis. The compound should be administered at a time when the hypothalamic-pituitary-adrenal axis is quiescent, i.e., in humans at 8 p.m. However, it could be administered between 8 a.m.–10 a.m., for example, when giving compounds such as AVP. When an immune/inflammatory mediator such as interleukin-1 is used, the immune inflammatory mediator would probably be administered in a dose of 0.1 $\mu$g/kg to 10 $\mu$g/kg of body weight, preferably 1 $\mu$g/kg to 5 $\mu$g/kg of body weight. When CRH is used, 1 $\mu$g ovine CRH per kg body weight is administered i.v. When AVP is used, 0.01 to 2.0 mI-U/kg/min is infused i.v. When a biogenic amine or analogue thereof such as quipazine is used, the compound would probably be administered in a dose of 0.01 to 1 mg of quipazine per kg of body weight, preferably 0.1 to 0.5 mg/kg of body weight. Doses for other biogenic amines or analogues thereof should be determined on a case-by-case basis.

After administration of the compound it is necessary to wait for a time sufficient to allow the compound to raise the glucocorticoid or ACTH level in the blood plasma of the patient before testing. Generally, it is necessary to wait at least 10 minutes before testing The glucocorticoid or ACTH level should be measured before the level returns to normal. The glucocorticoid or ACTH level may return to normal within 4 hours after administration of the compound. A preferred waiting period is 15 minutes to 2 hours after administration, more preferably 30 to 60 minutes after administration. If the hormone levels are significantly lower than (such as more than two standard deviations below) the mean established in normal individuals, then the patient has tested positive for possible susceptibility to inflammatory diseases.

The method is potentially useful for testing for inflammatory diseases including, but not limited to, arthritis, uveoretinitis, pneumonitis, encephalomyelitis, myocarditis, thyroiditis, nephritis, sialadenitis, adrenalitis, orchitis, multiple sclerosis and hepatic granulomatous diseases.

Various immune/inflammatory mediators may be used. Cytokines such as any one of the interleukins (interleukin-1 (IL-1), interleukin-2 (IL-2), interleukin-3 (IL-3), interleukin-4 (IL-4), interleukin-5 (IL-5) and interleukin-6 (IL-6)), interferons (alpha interferon, beta interferon and gamma interferon) or tumor necrosis factor (TNF) may be used in the test. Other cytokines such as epidermal growth factor (EGF), transforming growth factor-alpha and/or beta (TGF-alpha and/or TGF-beta) may also be used. Biogenic amines such as serotonin, norepinephrine, epinephrine, or dopamine may be used. In addition, analogs and agonists of these biogenic amines such as quipazine may also be used. Additional compounds which may be used include monoamine oxidase inhibitors such as tranylcypromine sulfate (30 mg/patient) or isocarboxazid (30 mg/patient) which increase endogenous levels of biogenic amines. Biogenic amine uptake inhibitors such as fluoxetine may also be used.

It is known that inflammatory mediators such as IL-1 cause an increase in plasma corticosterone and ACTH possibly by stimulating the hypothalamic-pituitary-adrenal (HPA) axis. The present invention is based on the finding that susceptibility to arthritis and other inflammatory diseases is related to lack of HPA axis responsiveness to inflammatory mediators and other compounds.

The present invention is also potentially useful as a guide for the treatment of arthritis with agents that may bypass the HPA defect by stimulating the HPA axis centrally or at multiple levels. Such drugs would include the drugs listed below:

Neurotransmitters/monoamines/neuroexcitatory agents:
  serotonin agonists/releasers/uptake inhibitors:
    quipazine
    1-metachloro-phenyl-piperazine (mCPP)
    fenfluoramine
    fluoxetine
  adrenergic agonists/antagonists/uptake inhibitors:
    idasoxan
    yohimbine
    methoxamine
    desmethylimipramine
    ritalin
  cholinergic agents:
    arecholine
    nicotine
  GABA agonists/antagonists:
    BCCM-beta carboline
    FG 7142 (Sandoz)
    RO 15788
  MAO inhibitors:
    MAO A:chlorgyline
    MAO B: phenylzine
    isocarboxazid
    tranylcypromine
  Dopamine uptake inhibitors/releasers
    buproprion
    amphetamine
  Excitatory amino acids/neuroexcitatory agents;
    glutamate
    cocaine
Neurohormones:
  rat/human corticotropin releasing hormone (CRH)
  corticotropin (ACTH)
  dexamethasone
  arginine vasopressin (AVP)
  thyroxin
  thyroid stimulating hormone (TSH)
  estrogen
  progesterone
  testosterone
  Diapid (Bissendorff, LHRH antagonist)

It may also provide a guide for determination of dosage and timing schedule of replacement steroids or other HPA axis hormones such as CRH or ACTH.

The above noted agents have been selected for possible treatment of inflammatory diseases such as rheumatoid arthritis because they represent a variety of classes of neuroactive agents which would be expected to activate the CRH and/or related arousal systems on a long-term basis (i.e., without inducing tolerance). Such an effect would correct the putative pathophysiological defect in rheumatoid arthritis and, hence, significantly ameloriate inflammatory and/or affective symptoms associated with this illness. Of the above-mentioned compounds, it is expected that 1-metachloro-phenyl-piperazine (mCPP) (an antidepressant), fluoxetine (an antidepressant), idasoxan (an antidepressant), nicotine, FG 7142 (Sandoz), MAO A:chlorgyline (an antidepressant), and MAO B:phenylzine (an antidepressant) are expected to be preferred compounds for further study.

These compounds will probably be administered in the same manner as recommended for their already known indications such as antidepressants. Specifically, these compounds should be administered in an amount effective to stimulate the HPA axis which would bypass the defect in the HPA axis. It is also expected that analogues and/or derivatives of the above compounds may be useful.

DETAILED DESCRIPTION OF THE INVENTION

Figure 1:
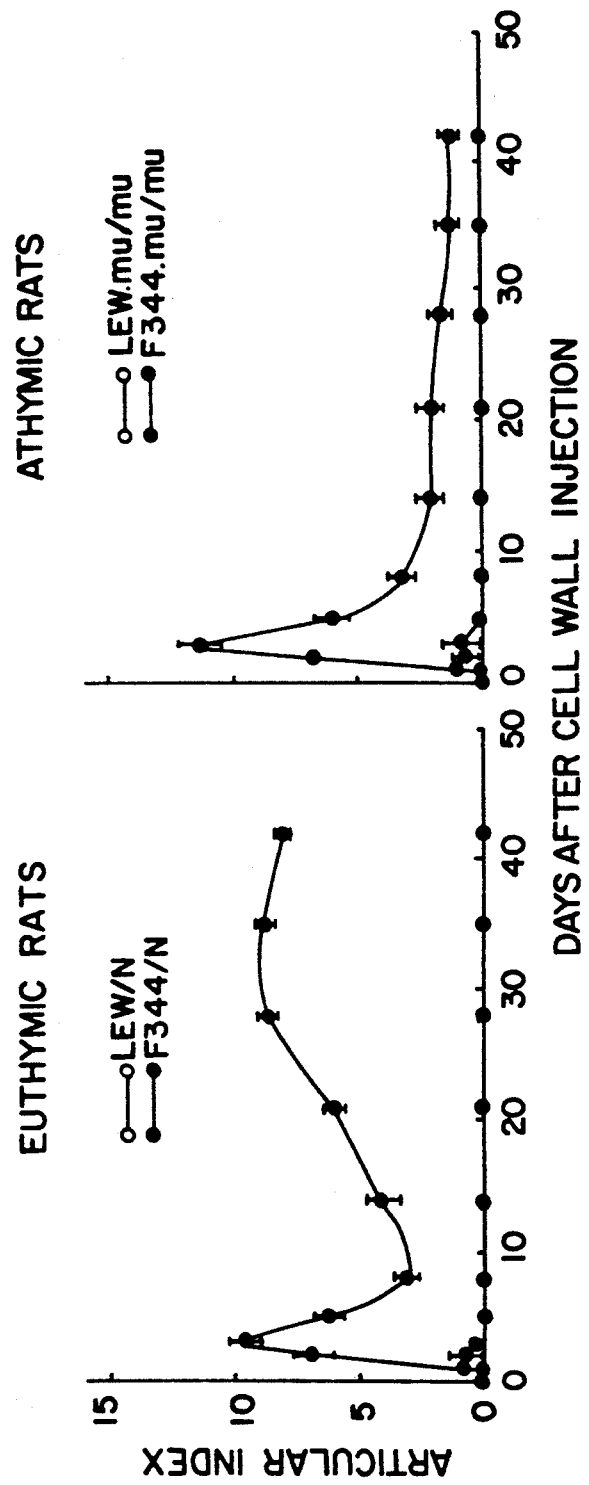
FIG. 1. Severity of arthritis post-streptococcal cell wall (SCW) injection in euthymic versus athymic LEW and F344 rats. Severity of arthritis was quantitated by articular index (maximum of 16) for up to 42 days following a single p. SCW injection. Data represent the mean ± S.E.M. for 5 rats per experimental group.

A single intraperitoneal injection of an aqueous suspension of Group A Streptococcal cell wall fragments (peptidoglycan-group specific polysaccharide) into LEW/N female rats induces severe, rapid onset, acute thymic-independent arthritis, followed by a chronic proliferative and erosive thymic-dependent arthritis. However, histocompatible F344/N female rats, along with several other histocompatible strains, develop only minimal, transient swelling of the hind paws (1, 2). Strain dependent differences in response to the cell walls are also noted in the degree of splenic hypertrophy, blood leukocytosis, and the development of hepatic granulomata. The development of severe inflammatory pathology in the LEW/N rat is not related to differences in the quantities, the sites of localization, or the duration of persistence of the cell wall fragments. In both LEW/N and F344/N rats, the cell walls localize to the spleen, liver, bone marrow and synovial blood vessels of the peripheral joints (1, 3, 4). LEW/N rats develop a more persistent inflammatory reaction at the sites of cell wall localization than do F344/N rats (5). In vitro analyses of various mononuclear cell responses to cell walls have not provided fundamental insights into the mechanisms underlying the marked susceptibility to streptococcal cell wall-induced disease in the LEW/N rats and resistance in F344/N rats, although small differences between strains have been noted (6-8, and Wilder et al, unpublished data).

Histologically, the earliest changes in the acute phase arthritis in LEW/N rats are synovial microvascular injury associated with increased endothelial cell Ia expression. This is rapidly followed by infiltration of Ia positive macrophages in the synovium (1). At all time points F344/N rats exhibit little or no inflammation compared to LEW/N rats. This difference in the degree of synovial macrophage and endothelial cell Ia expression, that parallels the development of arthritis, is the most striking immunohistological difference between the two strains. This difference is even observed in athymic LEW.rnu/rnu and F344.rnu/rnu rats. This suggests that there may be a factor or factors regulating both Ia expression and the acute thymic-independent phase of SCW arthritis, and that the difference in arthritis susceptibility between the two strains may be related to the presence of a down-regulator of Ia operative soon after injection of SCW in F344/N but not in LEW/N rats.

Corticosteroids are both potent endogenous down-regulators of Ia expression, and potent endogenous immunosuppressive and anti-inflammatory agents (9-13). Corticosterone is released early in the course of inflammation through stimulation of the HPA axis by inflammatory mediators such as endotoxin and interleukin-1 (IL-1) (14-23). Since SCW activate macrophages and stimulate release of IL-1, and are chemically related to endotoxin (bacterial lipopolysaccharide, LPS) (24), and since IL-1 is critical in maintaining the normal feedback loop between the immune system and the central nervous system (CNS) (11-23, 25-26), the early ACTH and corticosterone responses to SCW and IL-1 alpha in inbred F344/N and LEW/N rats and outbred HSD rats were compared. Since serotonin (5-HT) is also released from platelets during inflammation, and down-regulates Ia expression (27, 28), and since 5-HT pathways represent another route of hypothalamic-pituitary stimulation (29-31), the effect of the serotonin agonist, quipazine, on acute ACTH and corticosterone responses in F344/N, LEW/N and HSD rats was also compared. Furthermore, to evaluate the direct involvement of glucocorticoids in the observed SCW susceptibility of LEW/N rats and SCW resistance of F344/N rats, the ability of replacement doses of glucocorticoids to suppress the SCW susceptibility of the former and the ability of a potent glucocorticoid antagonist RU 486 to reverse the SCW resistance of the latter was examined.

DETAILED DESCRIPTION OF THE PREFERRED EMBODIMENT

Animals: One hundred gram, virus antibody free, female, inbred F344/N and LEW/N rats, and outbred Harlan-Sprague-Dawley (HSD) rats, purchased from Harlan Sprague Dawley (Indianapolis, Ind.), were acclimatized to 12 hour on-12 hour off light cycles, prior to intraperitoneal injection of various inflammatory mediators.

Drugs and inflammatory mediators: Group A Streptococcal cell wall peptidoglycan-group specific carbohydrate (SCW) was prepared in phosphate buffered saline (PBS), as previously described (1). It was injected at a concentration of 0.02 to 2 mg of cell wall rhamnose per rat. Recombinant human interleukin-1 alpha (IL-1 alpha): IL-1 alpha (32) was a generous gift from Drs. P. Kilian and P. Lomedico, (Hoffman-La Roche, Nutley, N.J.). It was injected at doses ranging from 0.1 to 5 μgm per rat. Specific activity ranged from $3-10^8$ to $2.5 \times 10^9$ Units/μgm. 1 unit of IL-1 activity was defined in the D10 cell bioassay, as previously described (32). Endotoxin levels in final concentrations injected were less than 0.0013 EU/100 μl. Quipazine was purchased from Sigma Chemical Company (St. Louis, Mo.). It was injected at doses ranging from 0.1 to 5 mg per rat. Dexamethasone for cell culture was purchased from Sigma Chemical Company (St. Louis, Mo.), and used in doses ranging from 0.01 μg to 100 μgm per rat. RU 486: The glucocorticoid receptor antagonist, RU 486, (33, Philibert, D., Deraedt, R., & Teutsch, G., (1981) Proc. VIII International Congress of Pharmacology, p. 668.) was a generous gift from Roussel-UCLAF (Paris, France). It was suspended in sterile normal saline for intraperitoneal (i.p.) injection, at doses ranging from 0.03 mg to 3 mg per rat. LY53857: The serotonin (5-hydroxytryptamine, 5-$HT_2$) antagonist, LY53857 (6-methyl-1-[1-methylethyl]ergoline-8-carboxylic acid, 2-hydroxy-1-methylpropy ester [Z]-2-butenedioate) (34), was a generous gift from Dr. M. Cohen, Lilly Research Laboratories, Eli Lilly and Co. (Indianapolis, Ind.). Rat/human corticotropin releasing hormone (CRH) was purchased from Peninsula Laboratories (Belmont, Calif.), and was used at doses ranging from 0.01 to 8 μgm per rat.

Hormone assays: Plasma corticosterone was quantitated by radioimmunoassay (35) kit purchased from Radioassay Systems Laboratories, Inc., Immunochem Corporation (Carson, Calif.). Adrenocorticotrophic hormone (ACTH) levels were determined by radioimmunoassay, as previously described (36). Rats were injected i.p. between 10 and 11 AM, and blood was collected from 30 minutes to 4 hours post-injection, for plasma ACTH and corticosterone measurements. Inter- and intra-assay control variability for corticosterone was 1.2% and 3.4% respectively; inter- and intra-assay control variability for ACTH was 8.0% and 2.8% respectively.

Severity of arthritis: Severity of arthritis was quantitated by articular index, performed by a single blinded observer, as previously described (2). Briefly, articular index is the sum of the severity of arthritis (scale 0–4, 4—most severe arthritis) of each of the limbs. Maximum articular index is 16.

Data analysis: A minimum of 5 rats per experimental group were studied, and experiments were repeated a minimum of 3 times. Data shown are mean ± standard error of the mean (S.E.M.) of each group. Experimental groups were compared to vehicle treated controls and to each other, and statistical significance between groups was determined by unpaired Student t test. Total ACTH and corticosterone released were calculated by integrating the areas under the curves, using the trapezoid rule.

RESULTS

Thymic-independent and thymic-dependent phases of LEW/N SCW induced arthritis FIG. 1 shows the repeat of an earlier experiment (1) in which the articular index (AI) was assessed in euthymic versus athymic LEW and F344 rats injected with SCW. Five animals in each group were treated with a single intra-peritoneal dose of SCW at day 0, and observed for 6 weeks. The arthritis induced in euthymic LEW/N rats is diphasic, with a rapid-onset acute inflammatory component developing as early as 24 hours after injection of SCW, and a later chronic component developing at 3 to 6 weeks post-injection. Athymic LEW.rnu/rnu rats do not develop the late phase arthritis, but do develop the early inflammatory component and a continued low grade chronic synovitis. The early phase of SCW arthritis in LEW rats is, therefore, thymic-independent, and the late phase is thymic-dependent. The very small percentage of euthymic and athymic F344 rats that develop mild arthritis develop only the early thymic-independent component, which rapidly resolves. The presence of a strain difference in the acute, thymic-independent phase of SCW arthritis in athymic LEW.rnu/rnu versus F344.rnu/rnu rats indicates that the thymic-independent phase of the arthritis is genetically regulated, and that the regulating factor or factors are operative very early in the disease.

Corticosterone responses to SCW, IL-1 aloha and quipazine in outbred HSD rats versus inbred F344/N and LEW/N rats Since, as discussed above, corticosterone is a potent down-regulator of Ia expression which is released early in the course of inflammation through stimulation of the HPA axis by inflammatory mediators (14-23), the early ACTH and corticosterone responses to SCW, IL-1 alpha and the serotonin (5-HT) agonist, quipazine, in inbred F344/N and LEW/N rats and outbred HSD rats were compared.

Figure 2:
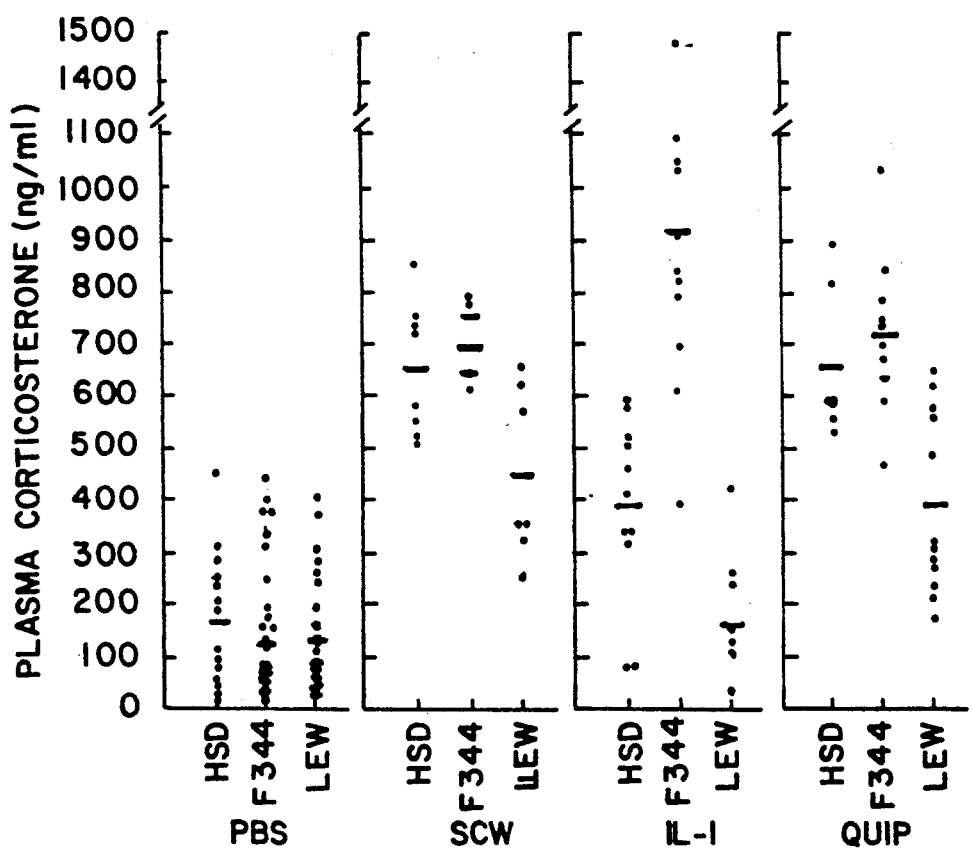
FIG. 2. Plasma corticosterone levels induced by SCW, IL-1 alpha, or quipazine in inbred F344/N and LEW/N rats, and in outbred HSD rats. Rats of each strain were injected i.p. with one mediator, as shown: SCW, (2 mg cell wall rhamnose), 1 $\mu$gm recombinant IL-1 alpha, mg quipazine or PBS control. Corticosterone was determined in plasma collected 60 minutes post-injection. Horizontal lines represent means of each group.
Figure 3A:
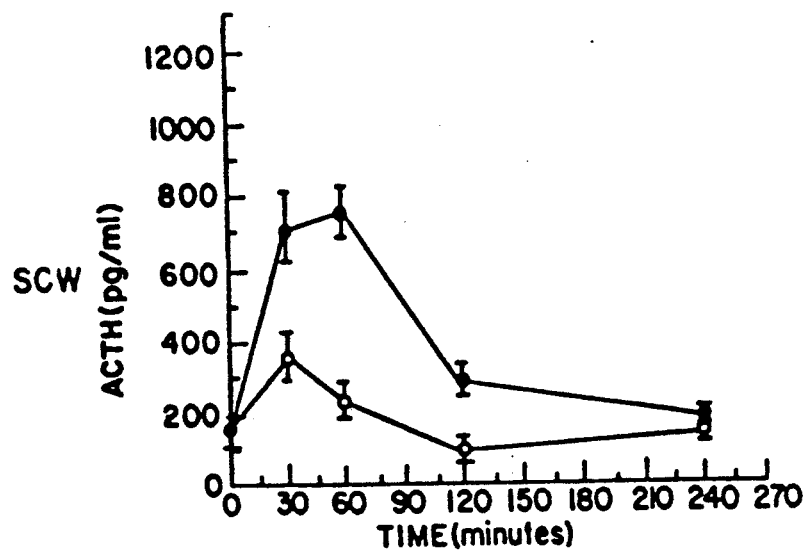
FIG. 3. Time course of plasma ACTH and corticosterone responses to SCW, (panels A and B); human recombinant IL-1 alpha (IL-1) (panels C and D); or quipazine (QUIP) (panels E and F) in F344/N (●) versus LEW/N (-○-) rats. Plasma ACTH and corticosterone were quantitated by radioimmunoassay at various time points up to 4 hours following i.p. injection of each agent shown. Data shown are mean ± S.E.M. of a minimum of 5 animals per experimental group.
Figure 3B:
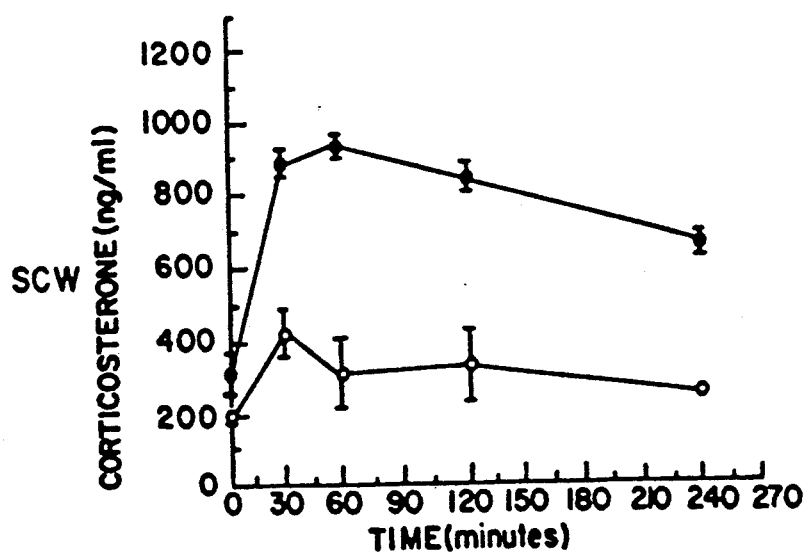
Figure 3C:
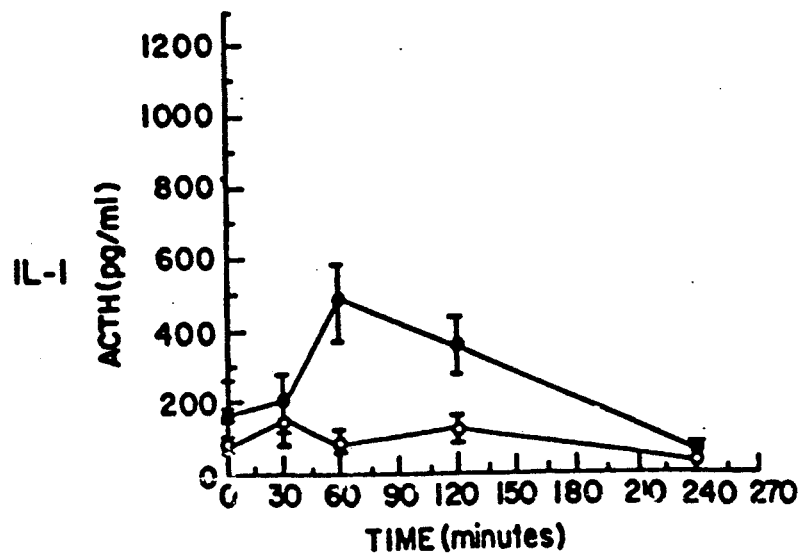
Figure 3D:
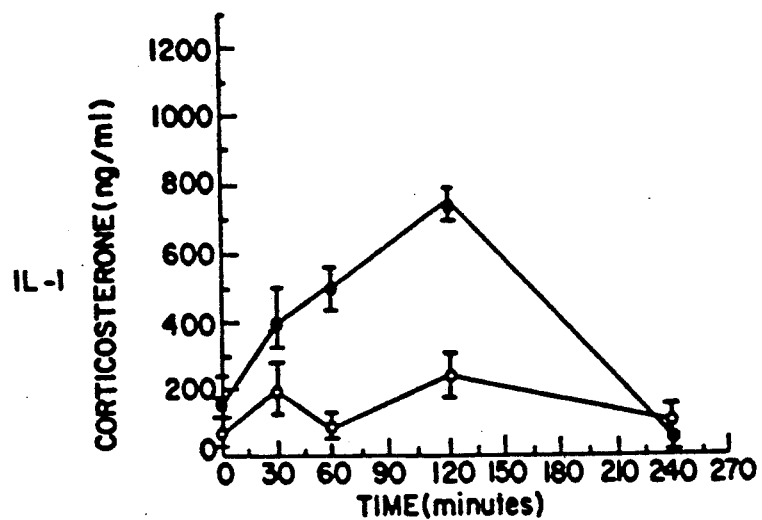
Figure 3E:
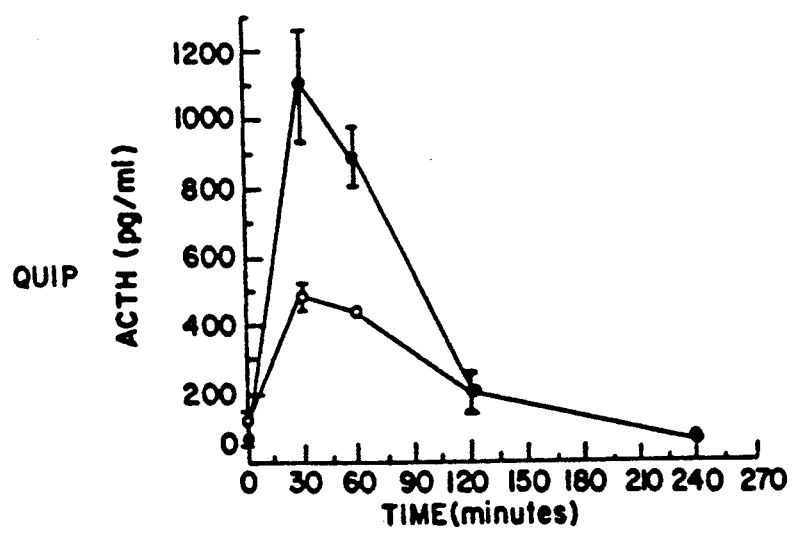
Figure 3F:
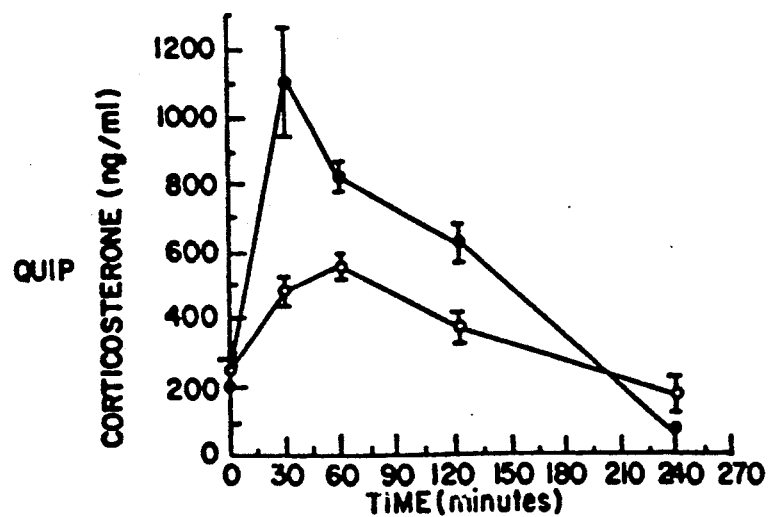
Figure 4A:
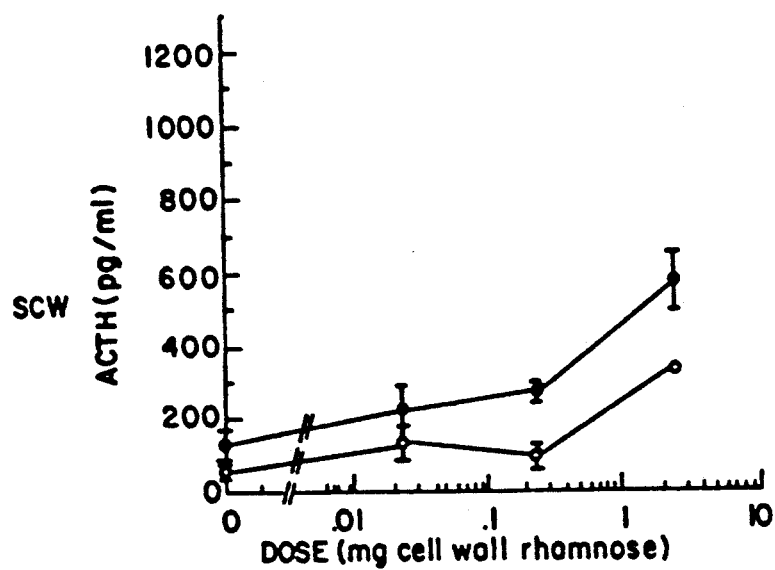
FIG. 4. Dose responses of plasma ACTH and corticosterone responses to SCW (panels A and B); human recombinant IL-1 alpha (IL-1) (panels C and D); or quipazine (QUIP) (panels E and F) in F344/N (●) versus LEW/N (-○-) rats. Various doses of mediators shown were injected i.p. and plasma ACTH and corticosterone were quantitated by radioimmunoassay 60 minutes post-injection. Data shown are mean ± S.E.M. of a minimum of 5 animals per group.
Figure 4B:
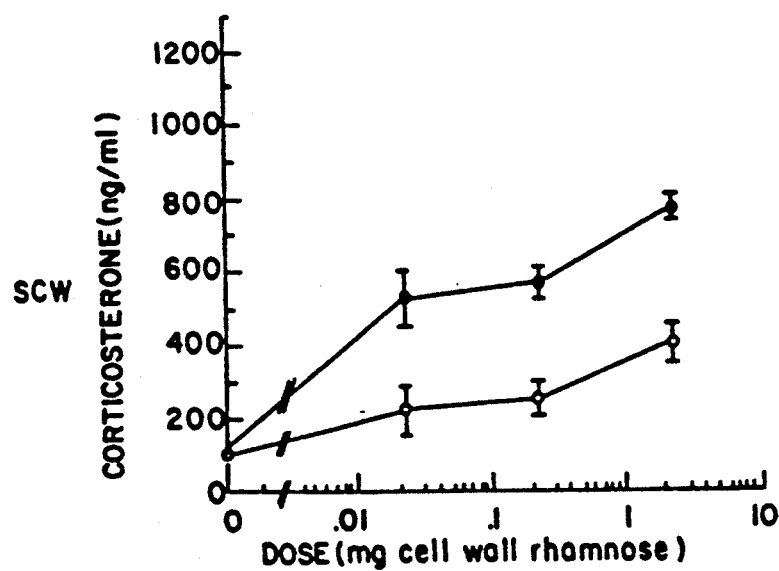
Figure 4C:
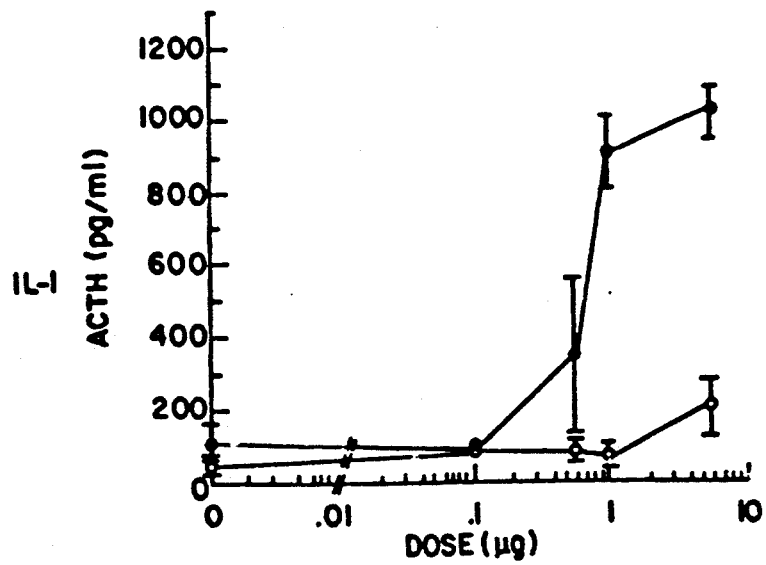
Figure 4D:
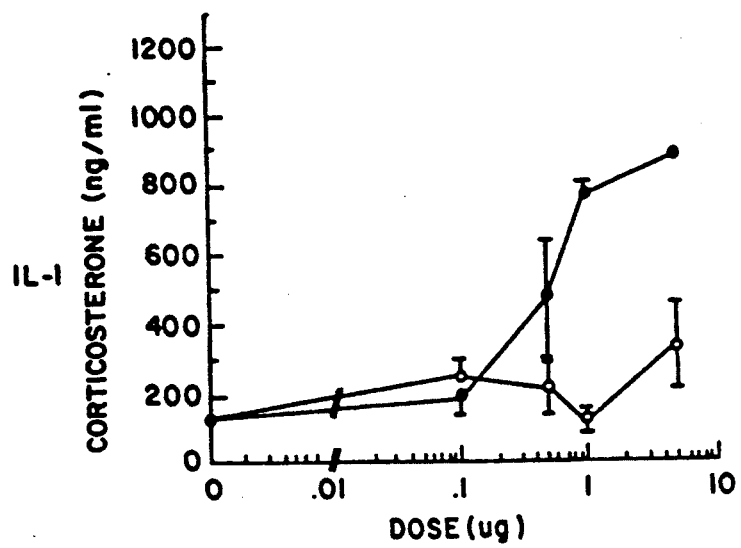
Figure 4E:
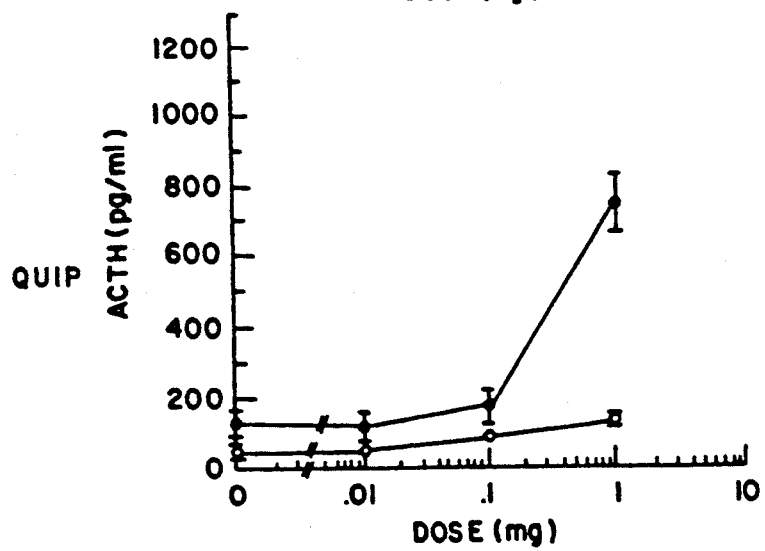
Figure 4F:
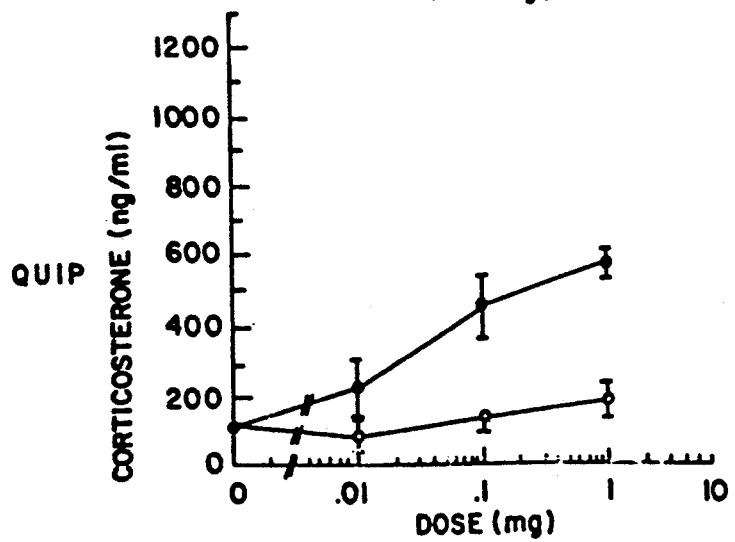

Intraperitoneal SCW, IL-1 alpha, and the serotonin (5-HT) agonist quipazine all induced marked plasma corticosterone responses in F344/N rats at one hour post i.p. injection (FIG. 2 and Table 1). In contrast, these agents induced only minimal (SCW, quipazine) or absent (IL-1 alpha) plasma corticosterone responses in LEW/N rats ($p<0.01$). Outbred HSD rats exhibited mean corticosterone responses intermediate between the low LEW/N and high F344/N responses. Corticosterone responses of HSD rats showed a wide spread, and fell into two groups: one overlapping the low LEW/N responses, and the other overlapping the high F344/N responses.

TABLE 1

Plasma corticosterone in PBS, SCW, IL-1 alpha or quipazine treated HSD, F344/N or LEW/N rats.

| | Plasma Corticosterone, ng/ml (mean ± S.E.M.) | | | |
|---|---|---|---|---|
| Strain | PBS | SCW | IL-1 alpha | Quipazine |
| HSD | 162.6 ± 33.4 | 656.1 ± 44.6 | 389.4 ± 54.1 | 656.8 ± 46.3 |
| F344/N | 130.7 ± 19.7 | 702.8 ± 32.7 | 913.7 ± 90.0 | 721.2 ± 43.9 |
| LEW/N | 130.2 ± 16.2 | 350.2 ± 31.3 | 162.5 ± 41.2 | 397.6 ± 51.2 |

Data represents mean ± S.E.M. of plasma corticosterone shown in FIG. 2. Plasma corticosterone was determined by radioimmunoassay of plasma collected 60 minutes post-i.p. injection of PBS, SCW (2 mg cell wall rhamnose/rat), IL-1 alpha (1 μgm/rat) or quipazine (1 mg/rat) in HSD, F344/N or LEW/N rats.

The one hour time point of corticosterone measurement and the doses of mediators used were those found to be associated with maximal corticosterone responses in time course and dose response experiments (FIGS. 3 and 4).

Time course kinetics of plasma ACTH and corticosterone responses to SCW, IL-1 alpha and cuipazine in LEW/N versus F344/N rats FIG. 3 shows that while plasma ACTH peaked at 30 to 60 minutes post-injection in both F344/N and LEW/N rats, the LEW/N plasma ACTH response to SCW, IL-1 alpha and quipazine was consistently lower than the F344/N response at al time points. Similarly, the LEW/N plasma corticosterone response was lower than the F344/N response at all time points. Total ACTH and corticosterone secreted over the entire time course in response to SCW, IL-1 alpha, or quipazine was significantly less in LEW/N rats than in F344/N rats (Table 2). In F344/N rats, compared to LEW/N rats, plasma ACTH increased more than 3 fold as much in response to IL-1 alpha; more than 2 fold as much in response to SCW, and more than 1.6 fold in response to quipazine. F344/N rats increased plasma corticosterone more than 2 fold in response to SCW and IL-1 alpha, and 1.4 fold in response to quipazine when compared to LEW/N rats.

TABLE 2

Total plasma ACTH and corticosterone secreted over 4 hours in response to SCW, IL-1 alpha or quipazine in LEW/N versus F344/N rats.

|  | F344/N | LEW/N | n | p | *F/L |
|---|---|---|---|---|---|
| Total ACTH (ng/ml × 240 min) (mean ± S.E.M.) | | | | | |
| SCW | 94.5 ± 4.7 | 40.3 ± 1.8 | 20 | <0.001 | 2.3 |
| IL-1 | 64.9 ± 5.4 | 20.4 ± 3.7 | 23 | <0.001 | 3.2 |
| Quipazine | 95.5 ± 12.0 | 57.3 ± 5.5 | 20 | <0.05 | 1.6 |
| Total Corticosterone (μg/ml × 240 min) (mean + S.E.M.) | | | | | |
| SCW | 184.9 ± 3.9 | 70.3 ± 11.9 | 32 | <0.001 | 2.6 |
| IL-1 | 104.5 ± 3.7 | 38.9 ± 7.9 | 33 | <0.001 | 2.7 |
| Quipazine | 119.6 ± 5.4 | 87.1 ± 4.4 | 20 | <0.01 | 1.4 |

*F/L = ratio of total ACTH or corticosterone secreted by F344/N (F) rats versus LEW/N (L) rats.

Data represent means ± S.E.M. of total plasma ACTH and corticosterone secreted by F344/N versus LEW/N rats in response to i.p. SCW (3 mg cell wall rhamnose/rat), IL-1 alpha (1 μg/rat), or quipazine (1 mg/rat). Data were derived, using the trapezoid rule, by calculation of the area under time course curves shown in FIG. 3.

Dose-responses of plasma ACTH and corticosterone to SCW, IL-1 alpha and quipazine in LEW/N versus F344/N rats FIG. 4 shows the plasma ACTH and corticosterone responses of LEW/N versus F344/N rats treated with varying doses of SCW, IL-1 alpha or quipazine. At all mediator doses tested, LEW/N rats had lower plasma ACTH and corticosterone levels than F344/N rats.

Figure 5A:
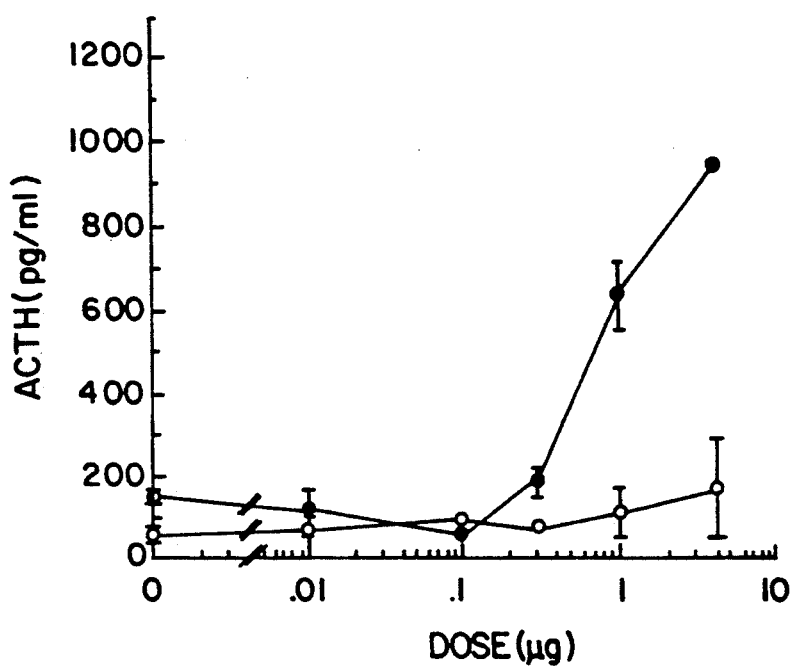
FIGS. 5a and 5b show dose response of plasma ACTH and corticosterone to various concentrations of human CRH. CRH was injected i.p., and plasma ACTH and corticosterone were measured by radioimmunoassay 60 minutes post injection. Data are mean ±S.E.M. of a minimum of 5 animals per experimental group.
Figure 5B:
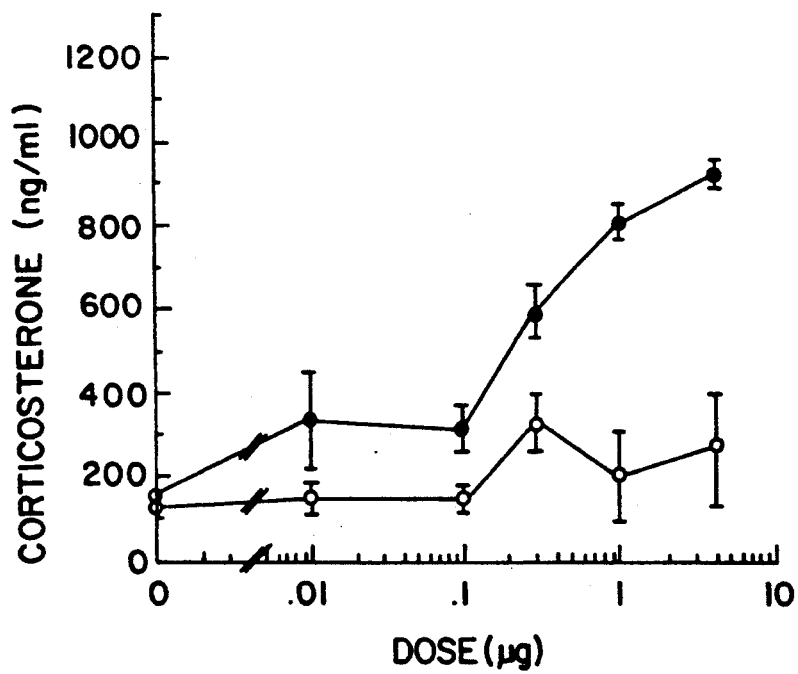

Plasma ACTH and corticosterone responses of LEW/N versus F344/N rats to rat/human CRH LEW/N ACTH and corticosterone responses to various doses of i.p. rat/human CRH were lower than F344/N responses (FIG. 5).

Pituitary, adrenal and thymus weights in F344/N versus LEW/N rats

Pituitary weights, although not significantly different, were greater in F344/N compared to LEW/N rats (Table 3). F344/N adrenal gland weights were slightly but significantly greater than adrenal gland weights from age-matched LEW/N rats (p<0.01). LEW/N thymus weights were significantly higher than F344/N thymus weights (p<0.01), in age-matched rats.

TABLE 3

Pituitary, adrenal and thymus weights in age-matched LEW/N and F344/N rats.

| Strain | (n) | Pituitary weight (mg) | (n) | Adrenal weight (mg) | (n) | Thymus weight (mg) |
|---|---|---|---|---|---|---|
| F344/N | (10) | 9.6 ± 0.5 | (27) | 15.6 ± 0.5 | (10) | 260.0 ± 8.9 |
| LEW/N | (13) | 8.5 ± 0.4 | (26) | 13.3 ± 0.7 | (10) | 307.3 ± 8.2 |
| P value | | N.S. | | <0.01 | | <0.01 |

Inhibition of SCW arthritis by dexamethasone treatment of LEW/N rats

Since corticosterone responses to SCW were clearly blunted in LEW/N rats, the effect of the corticosteroid, dexamethasone, on severity of arthritis in SCW treated LEW/N rats (Table 4) was. evaluated. Five animals per group were injected i.p. with SCW (2 mg cell wall rhamnose/rat) on day 0, together with various doses of dexamethasone. Dexamethasone treatment was continued for 72 hours at doses ranging from the physiologic replacement range of 0.5 μg twice daily (b.i.d.) or 1 μg once daily (QD) to doses in the pharmacologic range, (10–100 μg QD). Not only did dexamethasone doses in the pharmacologic range totally suppress the arthritis induced by SCW, but doses in the physiologic range (1 μg QD or 0.5 μg b.i.d.) also significantly suppressed the severity of arthritis as determined by arthritis index (A.I.) compared to SCW plus saline treated controls (p<0.05).

TABLE 4

Dexamethasone suppression of SCW arthritis in LEW/N rats (72 hrs).

| Dexamethasone dose (μg) | Incidence of arthritis | Severity of arthritis (mean A.I. + S.E.M.) |
|---|---|---|
| 0 | 5/5 | 8.3 ± 2.1 |
| 0.1 (b.i.d.) | 5/5 | 8.4 ± 1.8 |
| 0.5 (b.i.d.) | 4/5 | 3.4 ± 1.5* |
| 1.0 (QD) | 5/5 | 2.0 ± 0.5* |
| 10.0 | 0/4 | 0* |
| 100.0 | 0/5 | 0* |

*A.I. significantly less than A.I. of control animals (dexamethasone dose 0, saline only) (p < 0.05).

LEW/N rats were injected with a single dose of SCW (2 mg cell wall rhamnose/rat), followed by dexamethasone, at the doses indicated, or saline controls. Dexamethasone injections were given once (QD) or twice (b.i.d.) daily for a total of 72 hours, and severity of arthritis (A.I., articular index) was quantitated at 72 hours post-SCW injection by a single blinded observer.

Effect of the corticosterone receptor antagonist, RU 486, or the 5-HT$_2$ antagonist, LY53857, on F344/N treated with SCW Table 5 shows the effect of treatment of F344/N rats with SCW plus the corticosterone receptor antagonist RU 486, or SCW plus the 5-HT$_2$ antagonist LY53857, compared to either agent alone. Five animals per group were injected i.p. with SCW (2 mg cell wall rhamnose per rat) on day 0. Various doses of RU 486 were injected i.p. simultaneously with SCW, and the RU 486 was readministered once daily for up to 72 hours post-SCW injection. LY53857 treatment was begun simultaneously with SCW and continued twice daily for 72 hours Minimal mortality was observed in F344/N rats treated with SCW alone, and no mortality was observed in F344/N rats treated with RU 486 or LY53857 alone. Doses of RU 486 which had no effect alone (3 mg QD), were highly toxic when administered i.p. together with SCW, resulting in 100% mortality. Doses of RU 486 as low as 0.03 mg QD, when administered to SCW-treated rats, were still associated with significant inflammatory morbidity and mortality compared to controls RU 486 has previously been shown to exacerbate carrageenin-induced inflammation, without significant mortality (33). Increased mortality in the SCW-arthritis model was probably related to the severe peritonitis which developed in association with the combined i.p. administration of the two agents. At doses of RU 486 low enough to permit survival, surviving rats developed acute arthritis, in some cases of moderate severity, e.g., mean A.I. =4.5 at 0.3 mg RU 486 dose Concurrent treatment of F344/N rats with SCW and the 5-HT$_2$ antagonist LY53857 was not associated with significant mortality, but was associated with development of mild to moderate arthritis compared to control rats treated with either agent alone ($p<0.05$). Although not all dosing variables were explored, the data clearly show that blocking the effects of corticosterone or 5-HT in SCW treated F344/N rats resulted in severe or even fatal systemic inflammatory disease.

TABLE 5

Effects RU 486 or LY53857 on mortality and arthritis in F344/N rats treated with SCW.

| Agent(s) injected | Mortality | Incidence of arthritis in surviving rats | Severity of arthritis in surviving rats (A.I.) |
|---|---|---|---|
| SCW + saline | 2/15 | 1/13 | 0.2 |
| saline + RU 486 3.0 mg | 0/6 | 0/6 | 0 |
| SCW + RU 486 0.03 mg | 1/5* | 2/4 | 0.5 ± 0.3 |
| SCW + RU 486 0.1 mg | 2/5* | 1/3 | 0.3 ± 0.3 |
| SCW + RU 486 0.3 mg | 3/5* | 1/2 | 4.5 ± 4.5** |
| SCW + RU 486 1.0 mg | 4/5* | 0/1 | 0 |
| SCW + RU 486 3.0 mg | 5/5 | — | — |
| saline + LY53857 0.3 mg | 0/7 | 0/7 | 0 |
| SCW + LY53857 0.03 mg | 1/5 | 2/4 | 2 ± 1.2** |
| SCW + LY53857 0.3 mg | 0/5 | 2/5 | 2 ± 1.5 |

*Surviving rats receiving RU 486 plus SCW showed ruffled fur and peritoneal inflammation at necropsy.
**$p < 0.05$ compared to articular index (A.I.) of SCW plus saline treated F344/N rats were treated with a single injection of SCW (2 mg cell wall rhamnose/rat), followed by daily i.p. injections of RU 486, or twice daily i.p. injections of LY53857, at doses indicated. Control animals were treated with SCW plus saline, RU 486 plus saline, or LY53857 plus saline. Articular index was quantitated by a blinded observer at 72 hours post-SCW injection. Maximum A.I. is 16.

DISCUSSION

One of the earliest events that occurs in streptococcal cell wall injected LEW/N rats, and even in athymic nude LEW.rnu/rnu rats, is enhanced Ia expression on synovial endothelial cells. This develops concomitantly with the inflammatory proces, and the intensity of expression parallels the severity of the arthritis. In marked contrast, insignificant enhancement of Ia antigen expression develops in SCW-injected euthymic and athymic F344 rats (I). Corticosteroids are both potent endogenous down-regulators of Ia expression and potent endogenous immunosuppressive and anti-inflammatory agents (9–13). In the experiments reported here, it has been shown that acute corticosterone responses to SCW IL-1 alpha and quipazine are severely depressed in arthritis susceptible, high Ia-expressing LEW/N rats, compared to arthritis resistant low-Ia expressing F344/N rats. Outbred HSD rats, which exhibit an intermediate mean susceptibility to SCW induced arthritis with wide variability (2), also showed an intermediate mean and wide variability of corticosterone responses to these mediators. Furthermore, replacement of corticosterone with physiologic doses of dexamethasone significantly suppressed the severity of SCW arthritis in LEW/N rats. Conversely, antagonism of corticosterone in F344/N rats, with the corticosterone receptor antagonist RU 486, was associated with increased mortality, exacerbation of inflammation, and development of mild to moderate acute arthritis in this otherwise resistant strain. It is clear from these studies that, whether present on a genetic basis, as in LEW/N rats, or on a pharmacological basis, as in RU 486 treated F344/N rats, a deficiency in the corticosterone response to SCW is associated with development of susceptibility to SCW-induced inflammatory disease.

Elevation of corticosterone during inflammation results from stimulation of the hypothalamic-pituitary-adrenal (HPA) axis by inflammatory and immune mediators, such as endotoxin (bacterial lipopolysacchardie, LPS) and interleukin-1 (IL-1) (14–23). Since SCW (peptidoglycan-group specific polysaccharide) are chemically related to endotoxin, and stimulate the release of IL-1 from activated macrophages (24), SCW could increase corticosterone via IL-1 stimulation of the HPA axis. The studies presented here show that, in addition to depressed corticosterone responses to SCW, LEW/N rats have absent corticosterone responses to IL-1. Recent studies have shown that IL-1 stimulates the HPA axis at primarily the hypothalamic level by inducing CRH release (15–23). LEW/N rats have depressed ACTH responses which parallel the low corticosterone responses to SCW and IL-1, in contrast to F344/N rats which have higher ACTH and corticosterone responses. These initial findings suggest that the HPA axis defect in LEW/N rats is at either the hypothalamic and/or the pituitary level.

The smaller adrenal glands and the larger thymuses of LEW/N compared to F344/N rats, are also consistent with deficient HPA axis responses and chronic mild hyposecretion of corticosterone. LEW/N rats also have depressed ACTH and corticosterone responses to exogenous CRH. This could be secondary to inadequate priming of the anterior pituitary corticotroph by endogenous CRH or other ACTH secretagogues, or to some inherent defect of this cell. It is impossible from the data presented here to precisely define the site of the defect, whether hypothalamic or pituitary, particularly since chronic over- or understimulation of the HPA axis, from whatever cause, could result in secondary changes in baseline and stimulated levels of CRH, ACTH and corticosterone production, as well a secondary changes in adrenal and thymus sizes (13, 37). Further studies are required to determine the precise anatomical and molecular site of the lesion in LEW/N rats.

The observation that LEW/N rats are deficient in ACTH and corticosterone responses to the 5-HT agonist quipazine, as well as to IL-1 and SCW, suggests that the defect in these rats is not solely at the level of IL-I stimulation of the HPA axis. The greater LEW/N corticosterone response to quipazine compared to IL-1 alpha may be related to the multiple pathways through which 5-HT and 5-HT agonists stimulate the HPA axis (31, 38-40), perhaps allowing quipazine to partially bypass the LEW/N defect in IL-1 -hypothalamic-pituitary pathways. This hypothesis is supported by existing data indicating that serotonin represents both a major CRH and a potent ACTH secretagogue (31, 41, 42). The importance of 5-HT pathways in intactness of the inflammatory mediator—HPA axis loop and arthritis resistance is also suggested by the association of arthritis with LY53857 treatment of SCW-injected rats.

The greater LEW/N corticosterone and ACTH response to SCW compared to IL-1 may also be related to stimulation of the HPA axis at multiple levels by the many inflammatory mediators released by SCW, including IL-1, interleukin-2 (IL-2), tumor necrosis factor (TNF) and 5-HT. Although 5-HT does not cross the blood brain barrier, 5-HT released during inflammation could hypothetically directly stimulate pituitary release of ACTH (31, 41, 42). The physiologic relevance of such a potential route of 5-HT stimulation of the HPA axis is, however, not clear, since it would be dependent on adequate systemic concentrations of 5-HT reaching central sites.

Taken together, the experiments reported here show that LEW/N rats represent a strain of rats genetically deficient in ACTH and corticosterone responses to several inflammatory or stress mediators, including SCW and IL-1, and 5-HT agonist, quipazine, and exogenous CRH. In contrast, F344/N rats represent a histocompatible, relatively SCW arthritis-resistant strain with intact, potent ACTH and corticosterone responses to the same inflammatory or stress mediators. Responses of HSD rats represent those of an outbred population, covering a wide range of both inflammatory mediator-HPA axis ACTH and corticosterone responses and SCW-arthritis susceptibility.

LEW/N and F344/N rats, therefore, represent a unique animal model for a genetically determined defect in the CNS - inflammatory/immune system feedback loop. Whether of hypothalamic or pituitary origin, this defect is associated with increased susceptibility to arthritis in response to SCW, and could also contribute to the increased susceptibility to other experimentally-induced inflammatory diseases observed in LEW/N rats (43–50). The data, coupled with the markedly enhanced inflammatory disease in SCW-injected F344/N rats following pharmacologic interruption of the HPA axis, and suppression of arthritis severity in SCW-injected LEW/N rats following replacement doses of dexamethasone, provide strong evidence that arthritis susceptibility in the LEW/N rat, and resistance in the F344/N rat is regulated, at least partially, through corticosterone production and HPA axis responsiveness to inflammatory and possibly other stress mediators.

The data may also have implications for susceptibility to rheumatoid arthritis in humans. Rheumatoid arthritis is associated with a class II major histocompatibility complex (MHC) epitope that is shared amongst several different haplotypes. Studies examining the contribution of class II MHC (Ia) type to rheumatoid arthritis susceptibility have suggested that MHC type and sequence are only partially responsible for susceptibility to rheumatoid arthritis (51). Another, as yet undefined factor, perhaps one controlling regulation of Ia expression, may therefore contribute to susceptibility to rheumatoid arthritis. The data presented here are consistent with the concept that the additional factors regulating both Ia expression and susceptibility to arthritis are corticosteroids and responsiveness of the HPA axis to inflammatory and possibly other stress mediators. Several other lines of evidence support this concept. Rheumatoid patients are exquisitely sensitive to the disease-suppressing effects of low doses of corticosteroids; rheumatoid arthritis frequently remits during hypercortisolemic states, such as pregnancy, and exacerbates during hypocortisolemic states such as the post-partum period. These observations, coupled with our data, suggest that evaluation of hypothalamic-pituitary-adrenal axis responsiveness to inflammatory and possibly other stress mediators, in patients with rheumatoid arthritis, may provide new insights into the disease process.

Additional evidence indicates that susceptibility to streptococcal cell wall (SCW)-induced arthritis in the Lewis (LEW/N) rat, a model for human rheumatoid arthritis, is due, in part, to defective inflammatory and stress mediator-induced activation of the hypothalamic-pituitary-adrenal axis. To explore the mechanism of this defect, the functional integrity of the hypothalamic corticotropin releasing hormone (CRH) neuron in LEW/N rats was examined and compared to histocompatible, arthritis-resistant F344/N rats. In response to SCW or recombinant interleukin-1 alpha (rIL-1 alpha), LEW/N rats showed profoundly deficient paraventricular nucleus CRH mRNA levels, hypothalamic CRH content and CRH release from explanted hypothalami in organ culture. These data provide strong evidence that the defective LEW/N ACTH and corticosterone responses to inflammatory and other stress mediators, and LEW/N susceptibility to experimental arthritis, are due in part to a hypothalamic defect in the synthesis and secretion of CRH. The additional finding of deficient expression in LEW/N rats of the hypothalamic enkephalin gene, which is coordinately regulated with the CRH gene in response to stress, suggests that the primary defect is not in the CRH gene, but is rather related to its inappropriate regulation.

In response to intraperitoneal injections of Group A streptococcal cell wall peptidoglycan-polysaccharide (SCW), inbred Lewis (LEW/N) female rats develop severe proliferative and erosive arthritis which mimics human rheumatoid arthritis. Histocompatible Fischer (F344/N) rats, on the other hand, do not develop arthritis in response to the same SCW stimulus (1–8). In light of recent postulated evidence that inflammatory mediator-activation of glucocorticoid secretion is one. mechanism by which the immune response is appropriately regulated and restrained pituitary-adrenal responsiveness to SCW and other inflammatory stimuli in LEW/N and F344/N rats was previously explored (23, 52, 53). It was found that LEW/N rats have defective HPA axis responses to inflammatory and other stress mediators and that the response of F344/N rats to the same stimuli is intact, or above normal. Specifically, LEW/N rats, in contrast to F344/N rats, have markedly impaired plasma ACTH and corticosterone responses to intraperitoneally-injected SCW, to recombinant human interleukin-1 alpha (rIL-1 alpha), to the serotonin agonist, quipazine, and to synthetic rat/human corticotropin releasing hormine (CRH). In addition, LEW/N rats, compared to F344/N rats, have smaller adrenal glands and larger thymuses, consistent with chronic lack of stimulation by ACTH and corticosterone, respectively. Furthermore, arthritis and severe inflammation can be induced in otherwise SCW arthritis—resistant F344/N rats, by interruption of the HPA axis at its effector end-point, with the glucocorticoid receptor antagonist, RU 486. Taken together, these data indicate that LEW/N rats' pituitary and adrenal hyporesponsiveness to inflammatory and other stress mediators is a major factor contributing to their susceptibility to SCW arthritis and other experimental inflammatory diseases (43–50).

Pituitary ACTH hyporesponsiveness to stimuli can be primary, or secondary to lack of hypothalamic stimulation (36). In order to determine whether the impaired ACTH and corticosterone responses of LEW/N rats were hypothalamic in origin, the ability of streptococcal cell walls (SCW) or rIL-1 alpha to affect in vivo hypothalamic CRH mRNA expression in the paraventricular nucleus (PVN), in vivo hypothalamic CRH content, and in vitro hypothalamic CRH secretion in LEW/N and F344/N rats was compared. Results of these studies show that the LEW/N HPA axis defect involves the hypothalamus. In contrast to F344/N rats, neuronal synthesis and secretion of CRH within the PVN was markedly impaired.

Figure 6A:
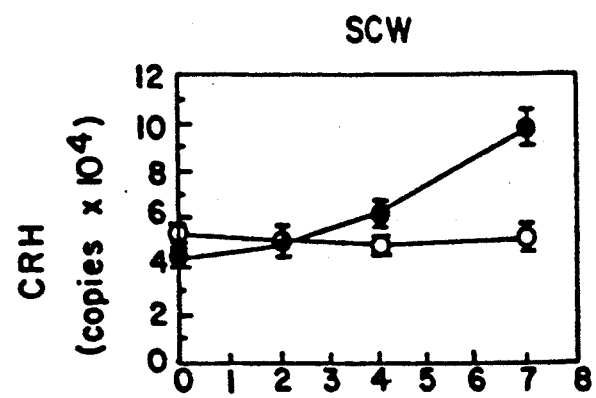
FIG. 6a through 6d. CRH (A) and enkephalin (B) transcript levels in the parvocellular neurons of the paraventricular nucleus (PVN) were increased by SCW administration in F344/N rats (●) but not in LEW/N rats (○). CRH (C) and enkephalin (D) transcript levels in the PVN were not increased by rIL-1 alpha administration in F344/N (●) or LEW/N (○) rats. F344/N and LEW/N rats were injected intraperitoneally with 2 mg cell wall rhamnose/100gm rat, or rIL-1 alpha, 1 $\mu$gm/100gm rat, and were sacrificed 0, 2, 4, and 7 hours later. In situ hybridization and determination of the number of copies of probe hybridized per section per PVN were performed as previously described (6, 7). CRH mRNA levels were clearly increased at 4 and 7 hours post-SCW injection in the F344/N rats, both in comparison with baseline and LEW/N levels (e.g., two-tailed T test, p<0.001 at 7 hours between strains). Although enkephalin mRNA levels rose above baseline in both strains in response to SCW administration, the F344/N response was greater than the LEW/N response (p<0.05). A minimum of 6 rats were used for each experimental condition, except the 2 hour time point, for which 4 rats were used. Bars represent S.E.M.
Figure 6B:
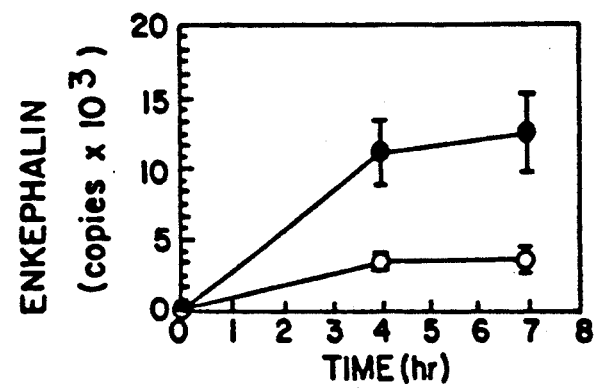

The influence of inflammatory mediators on hypothalamic expression of CRH mRNA was quantitated by in situ hybridization with a CRH probe in PVN sections from F344/N and LEW/N rats injected intraperitoneally with either SCW or rIL-1 alpha. 80-100 gm virus antibody-free, F344/N and LEW/N female rats (Harlan Sprague Dawley, Indianapolis, Ind.) were injected intraperitoneally with SCW (2 mg cell-wall rhamnose per 100 gm rat), or recombinant interleuki-1 alpha (rIL-1 alpha, 1 μgm/100 gm rat). Recombinant IL-1 alpha was a kind gift from Drs. P. Kilian and P. Lomedico, Hoffman-LaRoche., Nutley, N.J. Blood was immediately collected and used to determine plasma corticosterone and ACTH levels (35, 36). The brains were removed, and 4 mm coronal slices containing the PVN were frozen and stored at $-80°$ C. until 12 μm frozen sections were cut and thaw-mounted onto twice gelatin-coated slides. They were then processed for in situ hybridization with CRH or enkephalin probes and analyzed as previously described (54, 55, 56). The hybridizations were performed at 37° C. for 20–24 hours in 600 mM Tris-HCl (pH 7.5), 50% formamide, 4 mM EDTA, 0.1% sodium pyrophosphate, 0.2% SDS, 0.2 mg/ml heparin sulfate, and 10% dextran sulfate. The probes had specific activities of 10–15,000 Ci/mmol. Between 4 to 7 hours after injection of SCW, CRH mRNA levels increased significantly in F344/N PVN, but did not increase in LEW/N PVN (FIG. 6A). This lack of a CRH biosynthetic response to SCW in LEW/N rats could be secondary to a defect in the CRH gene or in steps leading to its activation. Coordinate regulation of the CRH and enkephalin genes in the PVN after application of two different stresses has been previously described (57, 58). In order to determine whether induction of the enkephalin gene by SCW was also defective in LEW/N rats, adjacent sections from the animals treated with SCW were examined for enkephalin expression by in situ hybridization. The response was much greater in the F344/N PVN than in the LEW/N PVN (FIG. 6B). These results suggest that a common pathway that activates the CRH and enkephalin genes in the PVN in F344/N and other normal rats (57, 58) is defective in LEW/N rats.

Figure 6C:
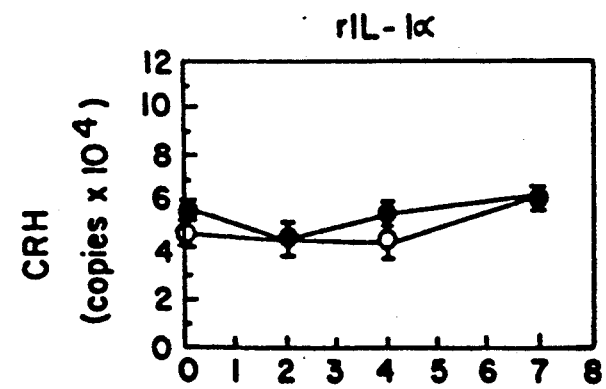
Figure 6D:
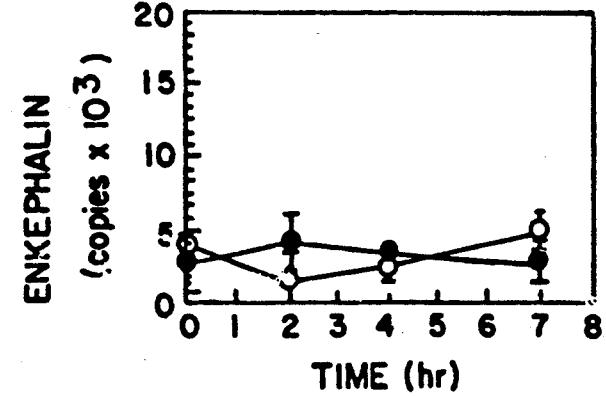

Bacterial endotoxin, lipopolysaccharide, (components of SCW) and IL-1 simulate the HPA axis (14–22, 59). Since SCW induce IL-1 release (24), IL-1 is one probable mediator of SCW HPA axis stimulation. Indeed, rIL-1 alpha did induce significant ($p<0.01$) increases in plasma corticosterone and ACTH in F344/N rats, compared to LEW/N rats (F344/N ACTH =480 pg/ml, LEW/N ACTH =70 pg/ml; F344/N corticosterone=488 ng/ml, LEW/N corticosterone=78 ng/ml, at one hour post-injection) (See preceding discussion). A similar single intraperitoneal injection of rIL-1 alpha (1 microgram per rat) however, did not significantly increase CRH mRNA or enkephalin mRNA in the PVN over baseline in either strain (FIGS. 6C and 6D). This discrepancy between the ability of rIL-1 alpha to augment plasma ACTH and corticosterone, and its inability to augment CRH mRNA levels in the PVN in F344/N rats, suggests that rIL-1 alpha, at the dose used, stimulates secretion, but not transcription of CRH. Alternatively, any increase in transcript levels induced by rIL-1 alpha may be below the level of sensitivity of the in situ hybridization assay. The increase of CRH mRNA levels induced by SCW, in contrast to the lack of CRH mRNA response to rIL-1 alpha, could be related to two mechanisms; the more sustained nature of the SCW stimulus compared to rIL-1 alpha, or the multiple factors released by SCW, which could stimulate the CRH neuron via multiple pathways.

Figure 7:
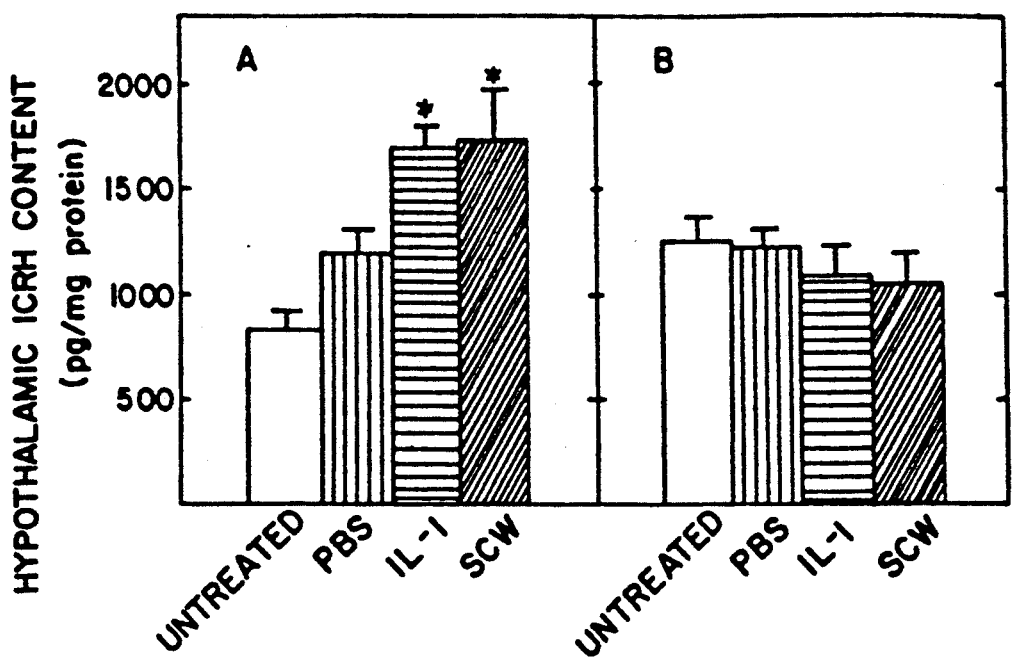
FIG. 7. Total hypothalamic immunoreactive CRH (iCRH) content in F344/N (A) and LEW/N (B) rats, measured 4 hours after intraperitoneal injection of various agents. F344/N (A) or LEW/N (B) rats were either untreated or were injected intraperitoneally with PBS, rIL-1 alpha, (1 μgm per rat), or SCW (2 mg cell wall rhamnose per rat), and iCRH hypothalamic content was quantitated by radioimmunoassay (10). A minimum of 10 rats per experimental condition was used. Statistical significance was determined by one-way ANOVA followed by Duncan's multiple range test. There was no significant difference between untreated and PBS-treated F344/N rats, nor between any treatment group of LEW/N rats by either criterion. Both rIL-1 alpha and SCW-treated F344/N hypothalami contained significantly more CRH than PBS or untreated F344/N hypothalami, and than treated or untreated LEW/N hypothalami (*=ANOVA p<0.0001, Duncan's multiple range p<0.05). Baseline levels of CRH in LEW/N hypothalami were not significantly different from baseline CRH levels in F344/N hypothalami by Duncan's multiple range test.

Total hypothalamic CRH content reflects the balance between CRH synthesis and secretion. Four hours after intraperitoneal injection of LEW/N or F344/N rats with SCW (2mg cell wall rhamnose per rat), recombinant IL-1 alpha (1 μgm per rat), or phosphate buffered saline (PBS, sterile, endotoxin free, GIBCO, Grand Island, N.Y.), rats were decapitated, and hypothalami were rapidly removed, quick-frozen on dry ice and extracted. Total immunoreactive CRH (iCRH) was quantitated by radioimmunoassay, as previously described (60). Hypothalamic immunoreactive CRH (iCRH) content, measured 4 hours after intraperitoneal injection of SCW, rIL-1 alpha, or phosphate buffered saline (PBS) is shown in FIG. 7. In F344/N rats, hypothalamic content of iCRH increased more than two fold over controls in response to either intraperitoneal SCW or rIL-1 alpha. iCRH content in PBS-injected and untreated animals was not significantly different. In contrast, iCRH content did not change in LEW/N rats injected with PBS, SCW or rIL-1 alpha, compared to untreated LEW/N rats. The lack of change in hypothalamic iCRH content of LEW/N rats in response to in vivo administration of SCW or rIL-1 alpha is consistent with the LEW/N rats' defective response of CRH mRNA to these mediators. The SCW-induced increase in hypothalamic iCRH in F344/N rats is consistent with their ability to increase CRH mRNA levels in response to SCW. rIL-1 alpha's capacity to increase hypothalamic iCRH content in F344/N rats, but not CRH mRNA levels in the PVN of these rats, suggests that IL-1 alpha may increase the rate or efficiency of CRH mRNA translation and/or post-translational processing without causing detectable increases in CRH transcript levels.

In order to determine whether IL-1 stimulation of CRH secretion is also defective in LEW/N rats, the ability of rIL-1 alpha to induce iCRH release in vitro from LEW/N versus F344/N hypothalamic explants was compared. Hypothalamic explants, obtained from untreated age-matched F344/N or LEW/N rats, were cultured in the presence of various concentrations of rIL-1 alpha and release of iCRH into the culture supernate was quantitated by radioimmunoassay. Hypothalamic explants were rapidly removed from untreated rats, as previously described (61, 62). The explants were incubated overnight at 37° C., 5% $CO_2$, in medium 199, (M199, GIBCO, Grand Island, N.Y.), with 0.1% bovine serum albumin (BSA, grade V, Sigma Chemicals, St.

Figure 8:
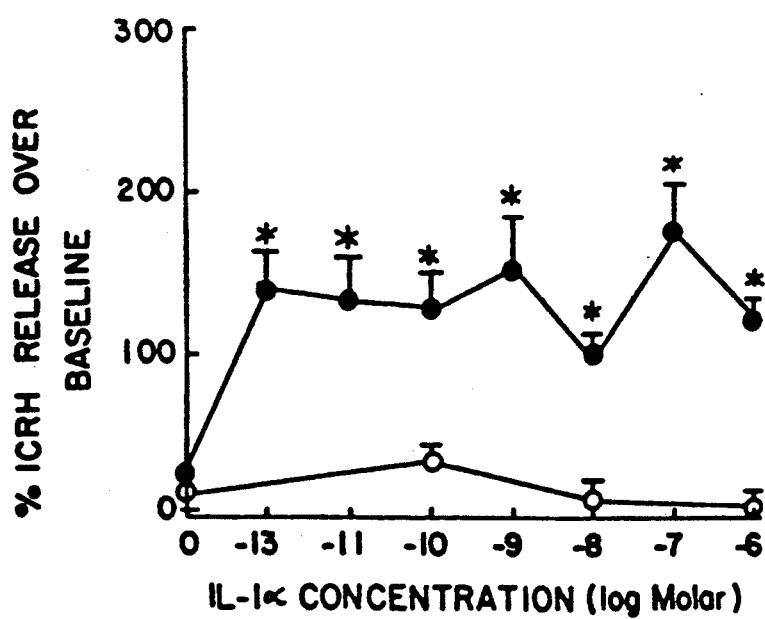
FIG. 8. Hypothalamic iCRH secretion from F344/N (●) versus LEW/N (○) rats stimulated in vitro with recombinant IL-1 alpha. Hypothalami from LEW/N or F344/N rats were stimulated for 20 minute periods in vitro with control medium or with rIL-1 alpha, at concentrations ranging from $10^{-13}M$ to $10^{-6}M$. iCRH in the culture medium was quantitated by radioimmunoassay (11). Hypothalami from F344/N rats showed an increase of 150% over baseline iCRH secretion, compared to a 10% increase over baseline by LEW/N hypothalami (*=p<0.001). Statistical significance was determined by Duncan's multiple range test. A minimum of 7 rats per experimental condition was used.

Louis, Mo.). The hypothalami, in 48 well tissue culture plates, were then serially transferred every 20 minutes through a series of six wells containing one of the following additives, in order: control M199 (3 wells, total 60 minutes); M199 plus recombinant IL-1 alpha ($10^{-13}$M to $10^{-6}$M; 2 wells, total 40 minutes); or 60 mM potassium chloride well, 20 minutes). Immunoreactive CRH (iCRH) was assayed directly in the media, by a sensitive radioimmunoassay, as previously described (63). Only results from viable hypothalami, represented by those with a >90% iCRH response to 60 mM KCl over basal values, were included in the analyses. FIG. 8 shows that rIL-1 alpha ($10^{-13}$M to $10^{-6}$M) induced a 150% increase in iCRH secretion over baseline from F344/N hypothalami, and no increase in iCRH secretion over baseline from LEW/N hypothalami.

As discussed previously, the LEW/N rats' defective ACTH and corticosterone responsiveness to inflammatory and other stress mediators is one critical factor in their susceptibility to SCW-induced arthritis. Our current findings suggest that the deficient LEW/N ACTH and corticosterone responses and associated susceptibility to arthritis are related to a lack of hypothalamic synthesis and secretion of CRH, and perhaps other stress hormones, in response to inflammatory and other stress mediators. The coordinate defect in LEW/N enkephalin mRNA synthesis in response to SCW provides evidence that the LEW/N rats' CRH biosynthetic defect is not specific to the CRH gene, but may result from a defect in its regulation. The present findings suggest a unique model for a mammalian autoimmune disease, in which a central nervous system defect results in an illness characterized by inadequate immune/inflammatory counter-regulation. Such a mechanism may also be relevant to human illnesses such as rheumatoid arthritis.

Arginine Vasopression Stimulation Test

There are currently two methods available to test the integrity of HPA axis responses in humans: the CRH stimulation test, and the arginine vasopression (AVP) stimulation test (Meller, W. H. et al, J. of Psychiatric Research, 21, No. 3, 269-277 (1987)). Further details of this test can be found in NIH Clinical Project No. 87-M-85a which is hereby incorporated by reference. Both these methods have been developed at the NIH Clinical Center, and have been extensively studied in diseases such as depression and Cushings' syndrome. The CRH stimulation test determines sensitivity of ACTH and cortisol responses to exogenous CRH, and therefore tests the integrity of pituitary corticotroph cells+ responses to stress. Since defective pituitary responsiveness to stress could be primary, or could be secondary to long-term hypothalamic defects as well, the CRH test also indirectly tests the integrity of hypothalamic responses to stress. A more direct measure of the integrity of hypothalamic CRH responses to stress is the AVP stimulation test. AVP synergizes with CRH in stimulating ACTH release. Decreased endogenous CRH would therefore result in decreased ACTH and cortisol secretion in response to exogenous AVP. Maximal ACTH and cortisol responses to AVP stimulation occur at 9 a.m., when CRH should be at its peak. Maximal ACTH and cortisol responses to CRH stimulation occur when CRH is at its nadir, at 4 p.m. An intravenous infusion of arginine vasopressin of 1.0 mIU/kg/min administered over a one hour period between 9:00 and 10:00 a.m. has been shown to have minimal side effects, and to maximally synergize with endogenous CRH in stimlating ACTH release. However, the infusion could be given at 8 p.m. to 9 p.m., depending on results of preliminary testing.

AVP Stimulation Test

Arginine vasopressin will be administered by an intravenous infusion of 1.0 mIU/kg/min of arginine vasopressin over a one hour period between 9:00 and 10:00 a.m. The infusions will be by means of a digitally controlled Extracorporeal Constant Infusion Pump, Model 2100. If any given dosage side effects such as nausea or gastrointestinal cramping occur, the infusion will be stopped immediately. Upon cessation of side effects, the infusion may again commence at a dose established to be free of side effects for a given individual. Side effects should be rare even at the maximal doses proposed for this study. In addition to the standard intracath placed for infusion of arginine vasopressin, blood will be drawn through a scalp vein needle in the contralateral arm, every 15 minutes before, during, and for two hours after the infusion. Eight cc's will be taken for every sample, and a total of 104 cc's will be taken for each infusion. Blood will be assayed for ACTH and cortisol, and in some cases also for other hormones such as beta-endorphin, growth hormone, prolactin and oxytocin.

Synthetic arginine vasopressin will be obtained from the Parke-Davis Company. Park-Davis markets a highly purified synthetic peptide with a sequence of naturally occurring arginine vasopressin and the commercial designation Aqueous Pitressin.

The components for use by the means described herein can be assembled as kits for use in accord with the teachings of the application. Such kits may contain the hypothalamic-pituitary-adrenal (HPA) axis stimulating drug, tracers such as I125 or an ELISA tracer, reagents specific for use in the assay chosen, antibodies to HPA axis hormone, and, for use as controls, standardized plasma. Any of the HPA axis hormones such as GABA agonists/antagonists, MAO inhibitors, Dopamine uptake inhibitors/releasers, Cholinergic agents, serotonin agonists/releasers/uptake inhibitors, adrenergic agonists/antagonistis/uptake named at page 5 are appropriate for use in kits in accord with the teachings of this disclosure. 1-metachloro-phenyl-piperazine (mCPP) is a particularly preferred stimulant.

REFERENCES

1. Wilder, R. L., Allen, J. B. & Hansen, C. (1987) J. Clin. Invest. 79, 1160–1171.
2. Wilder, R. L., Calandra, C. B., Garvin, A. J., Wright, K. D. & Hansen C. T. (1982) Arthritis Rheum. 25, 1064–1072.
3. Allen, J. B. & Wilder, R. L. (1985) Arthritis Rheum. 28, 1318–1319.
4. Anderle, S. K., Allen, J. B., Wilder, R. L., Eisenberg, R. A., Cromartie, W. J. & Schwab, J. H. (1985) Infect. Immun. 49, 836–837.
5. Allen, J. B., Calandra, G. B., & Wilder, R. L. (1983) Infect. Immun. 42, 796–801.
6. Wilder, R. L., Allen, J. B., Wahl, L. M., Calandra, G. B. & Wahl, S. M. (1983) Arthritis Rheum. 26, 1442–1072.
7. Ridge, S. C., Zabriskie, J. B., Osawa, H., Diamantstein, T., Oronsky, A. & Kerwar, S. S. (1986) J. Exp. Med. 164, 327–332.

8. Van den Broek, M. F., van Bruggen, J. C. J., van den Berg, W. & van den Putte, L. B. A. (1988) Arthritis. Rheum. 31, S91.
9. Snyder, D. S. & Unanue, E. R. (1982) J. Immunol. 129, 1803-1805.
10. Cupps, T. R. & Fauci, A. S. (1982) Immunol. Rev. 65, 133-155.
11. Munck, A., Guyre, P. M. & Holbrook, N.J. (1984) Endocr. Rev. 5, 25-44.
12. Sternberg, E. M. (1986) in The Year in Immunology, eds. Cruse, J. M. & Lewis, R. E., Jr. (S. Karger, Basel), Vol. 2, pp. 152-163.
13. Sternberg, E. M. (1988) in The Lymphocyte, Structure and Function, ed. Marchalonis, J. J., (Marcel Dekker, Inc., New York, N.Y., & Basel), pp. 1-54.
14. Fontana, A., Weber, E. & Dayer, J.-M. (1984) J. Immunol. 133, 1696-1698.
15 Woloski B. M. R. N. J., Smith, E. M., Meyer, W. J. III, Fuller, G. M. & Blalock, J. E. (1985) Science 230, 1035-1037.
16. Bernton, E. W., Beach, J. E., Holaday, J. W., Smallridge, R. C. & Fein, H. G. (1987) Science 238, 519-521.
17. Sapolsky, R., Rivier, C., Yamamoto, G., Plotsky, P. & Vale, W. (1987) Science, 238, 522-524.
18. Berkenbosch, F., Oers, J. V., Del Rey, A., Tilders, F. & Besedovsky, H. (1987) Science 238, 524-526.
19. Besedovsky, H., Del Rey, A., Sorkin, E. & Dinarello, C. A. (1986) Science 233, 652-654.
20. Uehara A., Gottschall, P. E., Dahl, R. R. & Arimura A. (1987) BBRC 146, 1286-1290.
21. Uehara, A., Gottschall, P. E., Dahl, R. R. & Arimura, A. (1987) Endocrinology 121, 1580-1582.
22. Calogero, A. E., Luger, R., Gallucci, W. T., Gold, P. W. & Chrousos, G. P. (1987) Endocrinology (Suppl.) 120, 271 (abstr. #1001).
23. Sternberg, E. M. (1988) in The Year in Immunology, ed. Cruse, J.M., (Karger, Basel) Vol. 4, pp. 1-13.
24. Wilder, R. L. (1987) Rheum. Dis. Clin. North Amer. 13, 293-306.
25. Pert, C. B., Ruff, M. R., Weber, R. J. & Herkenham, M., (1985) J. Immunol. 135, 820s-826s.
26. Farrar, W. L., Kilian, P. L., Ruff, M. R., Hill, J. M. & Pert, C. B. (1987) J. Immunol. 139, 459-463.
27. Sternberg, E. M., Trial, J. & Parker, C. W. (1986) J. Immunol. 137, 276-282.
28. Sternberg, E. M., Wedner, H. J., Leung, M. K. & Parker, C. W. (1987) J. Immunol. 138, 4360-4365.
29. Fuller, R. (1981) NeuroendoCrinol. 32, 118-127.
30. Cheung, A., Hall, T. R. & HarveY, S. (1987) J. Endocrinol. 113, 159-165.
31. Calogero, A. E., Bernardini, R., Margioris, A. N., Gallucci, W. T., Munson, P. J., Tamarkin, L., Tomai, T. P., Brady, L., Gold, P. W., & Chrousos, G. P. (1988) Peptides, in press.
32. Kilian, P. L., Kuffka, K. L., Stern, A. S., Woehle, D., Benjamin, W. R., Dechiara, T. M., Gubler, U., Farrar, J. J., Mizel, S. B. & Lomedico, P. T. (1986) J. Immunol. 136, 4509-4514.
33. Laue, L., Kawai, S., Brandon, D. D., Brightwell, D., Barnes, K., Knazek, R.A., Loriaux, D. L. & Chrousos, G. P. (1988) J. Steroid Biochem. in press.
34. Cohen, M. L., Fuller, R. W. & Kurz, K.D. (1983) J. of Pharmacol. Exp. Ther. 227, 327-332.
35. Gross, H. A., Ruder, J. J., Brown, K. S. & Lipsett, M. B. (1972) Steroids 20, 681-695.
36. Chrousos, G. P., Schulte, H. M., Oldfield, E. H., Gold, P. W., Cutler, Jr., G. B. & Loriaux, D. L. (1984) New Engl. J. Med. 310, 622-626.
37. Chrousos, G. P., Cutler, G. B. Jr. & Loriaux, D. L. (1983) Pharmacol. Ther. 20, 263-281.
38. Gibbs, D. M. & Vale, W. (19.83) Brain Res. 280, 176-179.
39. Hashimoto, K., Ohno, N., Murakami, J. J., Aoki, Y. & Takahara, J. (1982) J. Endocrinol. 93, 151-160.
40. Spinedi, E. & Negro-Vilar, A. (1983) Endocrinology 112, 1217-1223.
41. Larsen, G. L. & Hensen, P. M. (1983) Ann. Rev. Immunol. 1, 335-359.
42. Page I.H. (1968) in Serotonin, (Year Book Medical Publishers Inc., Chicago).
43. Kohashi, O., Kohashi, Y., Takahashi, T., Ozawa, A. & Shigematsu, N. (1986) Arthritis Rheum. 29, 547-553.
44. Griffiths, M. M. & DeWitt, C. W. (1984) J. Immunol. 132, 2830-2836.
45. Hill, J. L. & Yu D. T. (1987) Infect. Immun. 55, 721-726.
46. Beraud, E., Reshef, T., Vanderbark, A. A., Offner, H., Friz, R., Chou, C. H. J., Bernard, D. & Cohen, I. R. (1986) J. Immunol. 136, 511-515.
47. Caspi, R. R., Roberge, F. G., McCallister, M., ElSared, J., Kuwabara, T., Gery, I., Hanna, E. & Nussenblatt, R. B. (1986) J. Immunol. 136, 928-933.
48. Davis, J. K., Thorp, R. B., Maddox, P.A., Brown, M. B., Cassell & G. H. (1982) Infect. Immun. 36, 720-729.
49. Allen, J. B. & Wilder, R. L. (1987) Infect. Immun. 55, 674-679.
50. Lehman, T. J. A., Allen, J. B., Plotz, P. H. & Wilder, R. (1984) Arthrltis Rheum. 27, 939-942.
51. Todd, J. A., Acha-Orbea, H., Bell, J. I., Chao, N., Fronek, Z., Jacob, C. O., Mcdermott, M., Sinha, A. A., Timmerman, K., Steinman, L. & McDevitt, H. O. (1988) Science 240, 1003-1009.
52. Besedovsky, H. O., del Ray, A. and Sorkin, E., in Immunoreoulation. eds. N. Fabris, E. Garaci, J. Hadden and N.A. Mitcheson, Plenum Press, (New York), 315 (1983).
53. Munck, A., Guyre, P.M. and Holbrook, N.J., Endocr. Rev. 5, 25-44 (1984). 44 (1984).
54. Young III et al, W. S., NeurosCi. Lett. 70, 198-203 (1986).
55. Young III et al, W. S., Proc. Natl. Acad. Sci. (USA) 83, 9827-9831 (1986).
56. Lightman, S. L., Young III, W. S., J. Physiol. (Lond.) 394, 23-39 (1987).
57. Lightman, S. L., Young III, W. S., Nature 328, 643-645 (1987).
58. Lightman, S. L., Young III, W. S., J. Physiol. (Lond.) 403, 511-523 (1988).
59. Nakamura, H., Motoyoshi, S., and Kadokawa, T., Eur. J. Pharmacol. 151, 67-73 (1988).
60. Vale et al, W., Methods Enzymol. 103, 565-577 (1983).
61. Calogero et al, A. E., J. Clin. Invest. 82, 767-774 (1988).
62. Calogero et al, A. E., J. Clin. Invest., 82, 839-846 (1988).

What is claimed is:

1. A method for testing the susceptibility of a mammal to inflammatory diseases which comprises the steps of:

administering to a mammal a compound which is effective in stimulating the hypothalamic-pituitary-adrenal (HPA) axis; and measuring the level of at least one hormone secreted by the pituitary or adrenal glands of said mammal.

2. The method of claim 1, which comprises the steps of administering to a mammal of compound selected from the group consisting of cytokines, growth hormones, neuroendocrine hormones, biogenic amines, agonists of biogenic amines, analogs of biogenic amines, monoamine oxidase inhibitors, and biogenic amine uptake inhibitors; and measuring the level of glucocorticoids or adrenocorticotropic hormone in said mammal.

3. The method of claim 2, wherein said compound is a neuroendocrine hormone selected from the group consisting of corticotropin releasing hormone, arginine vasopressin (AVP) and thyroxin.

4. The method of claim 2, wherein said compound is a biogenic amine selected from the group consisting of serotonin, norepinephrine, epinephrine or dopamine.

5. The method of claim 2, wherein said compound is a biogenic amine agonist selected from the group consisting of quipazine, 1-metachloro-phenyl-piperazine (mCPP), idasoxan, yohimbine and ritalin.

6. The method of claim 2, wherein said compound is a monoamine oxidase inhibitor selected from the group consisting of isocarboxazid and tranylcypromine.

7. The method of claim 2, wherein said compound is a biogenic amine uptake inhibitor selected from the group consisting of fluoxetine and desmethylimipramine.

8. The method of claim 2, wherein said glucocorticoid is selected from the group consisting of cortisol and corticosterone.

9. The method of claim 2, wherein said measuring of glucocorticoids or adrenocorticotropic hormone is in blood plasma.

10. The method of claim 1 wherein said compound is a GABA agonist/antagonist selected from the group consisting of BCCM-beta carboline, FG 7142 and RO 15788.

11. The method of claim 2, wherein said inflammatory disease is arthritis.

12. The method of claim 1, wherein said inflammatory disease is arthritis, uveoretinitis, pneumonitis, encephalomyelitis, multiple sclerosis or hepatic granulomatas.

13. The method of claim 1, wherein said compound os interleukin-1, serotonin, corticotropin releasing hormone, AVP or quipazine and said hormone is cortisol, corticosterone or adrenocorticotropic hormone.

14. The method of claim 1, wherein the level of said hormones secreted by the pituitary or adrenal glands are measured 10 minutes to 4 hours after administration of said compound.

15. A method for testing the susceptibility of a mammal to arthritis which comprises the steps of:
administering to a mammal an amount of interleukin-1 or quipazine effective to stimulate the hypothalamic-pituitary-adrenal axis; and
measuring the level of adrenocorticotropic hormone or corticosterone in the plasma of said mammal between 10 minutes and 4 hours after administration of said interleukin-1 or quipazine.

16. The method of claim 15, wherein said mammal is a laboratory animal.

17. The method of claim 15, wherein said mammal is a human.

18. A method for treatment of inflammatory diseases which comprises the step of: administering to a patient suffering from an inflammatory disease a compound which stimulates the hypothalamic-pituitary-adrenal axis in an amount effective to stimulate said axis.

19. The method of claim 18, wherein said compound is administered to a patient suffering from rheumatoid arthritis.

20. The method of claim 18, wherein said compound is selected from the group consisting of cytokines, growth hormones, neuroendocrine hormones, biogenic amines, agonists or biogenic amines, analogs of biogenic amines, monoamine oxidase inhibitors, biogenic amine uptake inhibitors, and GABA agonists/antagonists.

21. The method of claim 20, wherein said compound is a neuroendocrine hormone selected from the group consisting of corticotropin releasing hormone, arginine vasopressin (AVP) and thyroxin.

22. The method of claim 20, wherein said compound is a biogenic amine selected from the group consisting of serotonin, norepinephrine, epinephrine or dopamine.

23. The method of claim 20, wherein said compound is a biogenic amine agonist selected from the group consisting of quipazine, 1-metachloro-phenyl-piperazine (mCPP), idasoxan, yohimbine and ritalin.

24. The method of claim 20, wherein said compound is a monoamine oxidase inhibitor selected from the group consisting of isocarboxazid and tranylcypromine.

25. The method of claim 20, wherein said compound is a biogenic amine uptake inhibitor selected from the group consisting of fluoxetine and desmethylimipramine.

26. The method of claim 20, wherein said compound is a GABA agonist/antagonist selected from the group consisting of BCCM-beta carboline, FG 7142 and RO 15788.

27. The method of claim 20, wherein said inflammatory disease is arthritis.

28. A kit comprising:
(1) a HPA axis stimulating agent: and
(2) reagents for measuring a HPA axis hormone response.

29. The kit of claim 28 further comprising a tracer.

30. The kit of claim 28 further comprising antibodies to the HPA axis hormone.

31. The kit of claim 28 wherein said reagents for measuring the HPA axis hormone response comprise reagents for an ELISA test.

32. The kit of claim 28 wherein the stimulating agent is a GABA agonist/antagonist.

33. The kit of claim 30 further comprising a standardized plasma as a control.

34. The kit of claim 29, wherein said tracer is I125.

35. The kit of claim 28, wherein said stimulating agent is selected from the group consisting of cytokines, growth hormones, neuroendocrine hormones, biogenic amines, agonists of biogenic amines, analogs of biogenic amines, monoamine oxidase inhibitors, and biogenic amine uptake inhibitors.

36. The kit of claim 35, wherein said stimulating agent is a neuroendocrine hormone selected from the group consisting of corticotropin releasing hormone, arginine vasopressin (AVP) and thyroxin.

37. The kit of claim 35, wherein said stimulating agent is a biogenic amine selected from the group consisting of serotonin, norepinephrine, epinephrine or dopamine.

38. The kit of claim 35, wherein said stimulating agent is a biogenic amine agonist selected from the group consisting of quipazine, 1-metachloro-phenyl-piperazine (mCPP), idasoxan, yohimbine and ritalin.

39. The kit of claim 35, wherein said stimulating agent is a monoamine oxidase inhibitor selected from the group consisting of isocarboxazid and tranylcypromine.

40. The kit of claim 35, wherein said stimulating agent is a biogenic amine uptake inhibitor selected from the group consisting of fluoxetine and desmethylimipramine.

41. The kit of claim 32, wherein said GABA agonist-/antagonist is selected from the group consisting of BCCM-beta carboline, FG 7142 and RO 15788.